(12) United States Patent
Uriarte et al.

(10) Patent No.: US 11,963,498 B2
(45) Date of Patent: *Apr. 23, 2024

(54) SORGHUM PLANTS HAVING A MUTANT POLYNUCLEOTIDE ENCODING THE LARGE SUBUNIT OF MUTATED ACETOHYDROXYACID SYNTHASE PROTEIN AND INCREASED RESISTANCE TO HERBICIDES

(71) Applicant: Advanta Holdings BV, Breda (NL)

(72) Inventors: Vicente Trucillo Uriarte, Buenos Aires (AR); Andrés Daniel Zambelli, Buenos Aires (AR); Marcos Kaspar, Buenos Aires (AR); Pedro Alejandro Pardo, Venado Tuerto (AR)

(73) Assignee: Advanta Holdings BV, Breda (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/584,313

(22) Filed: Sep. 26, 2019

(65) Prior Publication Data
US 2020/0015445 A1 Jan. 16, 2020

Related U.S. Application Data

(63) Continuation of application No. 13/822,276, filed as application No. PCT/EP2012/056352 on Apr. 5, 2012, now Pat. No. 10,485,195.

(51) Int. Cl.
| | | |
|---|---|---|
| *A01H 6/46* | (2018.01) | |
| *A01H 1/04* | (2006.01) | |
| *A01H 5/10* | (2018.01) | |
| *C12N 9/10* | (2006.01) | |
| *C12N 9/88* | (2006.01) | |
| *C12N 15/82* | (2006.01) | |
| *C12Q 1/6895* | (2018.01) | |

(52) U.S. Cl.
CPC .............. *A01H 6/4666* (2018.05); *A01H 5/10* (2013.01); *C12N 9/1022* (2013.01); *C12N 9/88* (2013.01); *C12N 15/8274* (2013.01); *C12N 15/8278* (2013.01); *C12Q 1/6895* (2013.01); *C12Y 202/01006* (2013.01); *C12Q 2600/156* (2013.01)

(58) Field of Classification Search
CPC .................. C12N 15/8274; C12N 15/8278
See application file for complete search history.

(56) References Cited

U.S. PATENT DOCUMENTS

| 5,378,824 A | 1/1995 | Bedbrook et al. |
| 5,859,348 A | 1/1999 | Penner et al. |
| 2003/0097692 A1 | 5/2003 | Jander et al. |
| 2008/0216187 A1 | 9/2008 | Tuinstra et al. |
| 2009/0205064 A1 | 8/2009 | Schopke et al. |
| 2010/0248965 A1 | 9/2010 | Hacker et al. |
| 2010/0287641 A1* | 11/2010 | McElver ............ C12N 15/8278 435/6.13 |
| 2011/0023161 A1* | 1/2011 | Tuinstra ......... C12Y 202/01006 800/278 |

FOREIGN PATENT DOCUMENTS

| JP | 2009-504137 A | 2/2009 |
| JP | 2010-523103 A | 7/2010 |
| JP | 2010-523123 A | 7/2010 |
| WO | WO03014356 A1 | 2/2003 |
| WO | WO2005020673 A1 | 3/2005 |
| WO | WO2006060634 A2 | 6/2006 |
| WO | WO2007005581 A2 | 1/2007 |
| WO | WO2007149069 A2 | 12/2007 |
| WO | WO2008124431 A1 | 10/2008 |
| WO | WO2008124495 A2 | 10/2008 |
| WO | WO2009031031 A2 | 3/2009 |
| WO | WO2009115237 A1 | 9/2009 |
| WO | WO2010037061 A1 | 4/2010 |

OTHER PUBLICATIONS

Hernández, María J., et al. "Target-site resistance to nicosulfuron in Johnsongrass (*Sorghum halepense*) from Chilean corn fields." Weed Science 63.3 (2015): 631-640. (Year: 2015).*
Currie, Randall S., Chae S. Kwon, and Donald Penner. "Magnitude of imazethapyr resistance of corn (*Zea mays*) hybrids with altered acetolactate synthase." Weed Science 43.4 (1995): 578-582. (Year: 1995).*
Dexter, 2001, Sugarbeet Res. Ext. Rep 32: 3-34.
Li et al., A Mutation at the Ala122 Position of Acetohydroxyacid Synthase (AHAS) Located on Chromosome 6D of Wheat: Improved Resistance to Imidazolinone and a Faster Assay for Marker Assisted Selection, Molecular Breeding, 2008, vol. 22, No. 2, p. 217-225.
Cross et al., Targeted Mutagenesis in Sorghum Using an Improved High-Throughput Screening Platform—A Reverse Genetics Strategy to Complement the Sorghum Genomics Effort, Centre for Plant Conservation Genetics Papers, 2006, p. 275.

(Continued)

Primary Examiner — Weihua Fan
(74) Attorney, Agent, or Firm — Rudy J. Ng; Bret E. Field; Bozicevic, Field & Francis LLP

(57) ABSTRACT

A sorghum seed comprising in its genome at least one polynucleotide encoding a polypeptide having an alanine to tyrosine substitution at position 93 of the sorghum AHAS protein large subunit. The plant has increased resistance to one or more herbicides, for example from the imidazolinone group, as compared to wild-type sorghum plants. The sorghum plant may comprise in its genome, one, two, three or more copies of a polynucleotide encoding a mutated large subunit of sorghum AHAS or a sorghum AHAS polypeptide of the invention. In this context, the sorghum plant may be tolerant to any herbicide capable of inhibiting AHAS enzyme activity. For example, the sorghum plant may be tolerant to herbicides of the imidazolinones type, such as imazethapyr, imazapir, and imazapic or to herbicides of the sulfonylurea group.

1 Claim, 8 Drawing Sheets
Specification includes a Sequence Listing.

(56) References Cited

OTHER PUBLICATIONS

Xin et al., Applying Genotyping (TILLING) and Phenotyping Analyses to Elucidate Gene Function in a Chemically Induced Sorghum Mutant Population, BMC Plant Biology, 2008, vol. 8, No. 1, p. 103.
Zhu et al., Engineering Herbicide-Resistant Maize Using Chimeric RNA/DNA Oligonucleotides, Nature Biotechnology, 2000, vol. 18, No. 5, p. 555-558.
Kochevenko et al., Chimeric RNA/DNA Oligonucleotide-Based Site-Specific Modification of the Tobacco Acetolactate Syntase Gene, Plant Physiology, 2003, vol. 132, No. 1, p. 174-184.
Lusser et al., Deployment of New Biotechnologies in Plant Breeding, Nat Biotechnol., 2012, vol. 30, No. 3, p. 231-239.
Marton et al., Nontransgenic Genome Modification in Plant Cells, Plant Physiology, 2010, vol. 154, No. 3, p. 1079-1087.
Powles et al., Evolution in Action: Plants Resistant to Herbicides, Annual Review of Plant Biology, 2010, vol. 61, No. 1, p. 317-347.
Roso et al., Regional Scale Distribution of Imidazolinone Herbicide-Resistant Alleles in Red Rice (*Oryza sativa* L.) Determined Through SNP Markers, Field Crops Research, 2010, vol. 119, No. 1, p. 175-182.

\* cited by examiner

FIG. 2A

```
ADV-IMI-R   (828)   1101
80237      (1101)   GGGAAGAATTGAGGCTTTTGCAAGCAGGCTAAGATTGTGCACATTGATATTGATCCCGCTGAGATTGCAAGAACAAGCAGCCACATGTCTCCATCTGTG
                    GGGAAGATTGAGGCTTTTGCAAGCAGGCTAAGATTGTGCACATTGATTGATTGATCCCGCTGAGATTGATCCCGCTGAAGCAAGCAAGCACATGTCCATGTCCATCTGTG
                    1201                                                                                          1300
ADV-IMI-R   (928)   CAGACGTTAAGCTTGCTTTGCATGGGCCATGCAGGAAGTCTCTTCTGGAAGGAAGCACATCAAGAGGAAGAGCTTGACTTGGCTCATGGCAAGCTGAGTTGGATCA
80237      (1201)   CAGACGTTAAGCTTGCTTTGCATGGGCCATGCAGGGAGTCTCTTCTGGAAGGAAGCACATCAAGAGAAGAGCTTGACTTGGCTCATGGCAAGCTGAGTTGGATCA
                    1301                                                                                          1400
ADV-IMI-R  (1028)   GCAGAAGAGAGAGAGAGTTCCCCCTTGGGTATAAAACTTTTGATGACGAGATCCAGCCACACATATGCTATTCAGGTTCTATTCAGTTCAGTTGACAAAAGGGGAGGCC
80237      (1301)   GCAGAAGAAGAGAGAGAGTTCCCCCTTGGGTATAAAACTTTTGATGACGAGATCAGCAGCCACACATATGCTATTCAGTTCTATTCAGTTGAGCTGACAAAGGGGAGGCC
                    SbAHAS-F4                                                                                     1500
ADV-IMI-R  (1128)   ATCATTGCCACAGGTGTTGGGCAGCACCAGATGTGGGCGGCAGCACAGTACTACACTTACAAGCGGCCAAGGCAGTGGTTGTCTTCAGCTGTTGGGCTA
80237      (1401)   ATCATTGCCACAGGTGTTGGGCAGCACCAGATGTGGGCGGCAGCACAGTACTACACTTACAAGCGGCCAAGGCAGTGGTTGTCTTCAGCTGTGGTCTTCAGCTGTTGGGCTA
                    SbAHAS-R3                                                                                     1600
ADV-IMI-R  (1223)   TGGGATTTGGTTTGCCCGTGCTCTGCTGCGCTGCCGCTGGGCCTGTGCCCAACCCAGTATCACTGTTGTTGACATGACGGAGATGGTAGCTTCCTCATGAACATTCA
80237      (1501)   TGGGATTTGGTTTGCCCGTGCTCTGCTGCGCTGCCGCTGGGCCTGTGCCCAACCCAGTATCACTGTTGTTGACATGACGGAGATGGTAGCTTCCTCATGAACATTCA
                    SbAHAS-F5                                                                                     1700
ADV-IMI-R  (1328)   GGAGCTAGCTATGGATCCGAATTGAGAACCTCCCAGTGAAGGTCTTTGTTCTGTCTAAAACAACCAGCAGCAACCTGGGAATGGTGGTGCACTGGGAGGACAGGTTCTAT
80237      (1601)   GGAGCTAGCTATGGATCCGAATTGAGAACCTCCCAGTGAAGGTCTTTGTTGTCTAAAACAACCAGCAGCAACCTGGGAATGGTGGTGCACTGGGAGGACAGGTTCTAT
                                                                                                                  1800
ADV-IMI-R  (1428)   AAGGCCAATAGAGCACACACATACTTGGGAAACCCAGAGCAATGAGAATGAGATATATCCAGATTTCGTGACAATTGCCAAAGGGTTCAACATTCCAGCAG
80237      (1701)   AAGGCCAATAGAGCACACACATACTTGGGAAACCCAGAGCAATGAGAATGAGATATATCCAGATTTCGTGACAATTGCAACATTCCAGCAG
                                                                                                                  1900
ADV-IMI-R  (1528)   TCCGTGTGACAAAGAAGAGAGCGAAGTCCATCGCAGTCCAGCTCCAGGGCCAGGGCCATACTCTTGGATATAATCGTCCCGCACCAGGAGCA
80237      (1801)   TCCGTGTGACAAAGAAGAGAGCGAAGTCCATCGCAGTCCAGCTCCAGGGCCAGGGCCATACTCTTGGATATAATCGTCCCGCACCAGGAGCA
                    SbAHAS-R4                                                                                     2000
                                                                                                           Stop Codon
ADV-IMI-R  (1628)   TGTGTTGCCTATGATCCCTAGTGGTGGGGCTTTCAAGGATGATGATCCTGATGGTCCAGGACTGTGTATTGATCTAAATTTCAGCAGTCAGATGCACATCTC
80237      (1901)   TGTGTTGCCTATGATCCCTAGTGGTGGGGCTTTCAAGGATGATGATCCTGATGGTCCAGGACTGTGTATTGATCTAAATTTCAGCAGTCAGATGCACATCTC
                                                                                                                  2100
ADV-IMI-R  (1728)   CCTGCCTTCTTTCTTTGACATGCATGCATGTACTCTGTTATGTGATGGTAAATCTTAAGTAGTTCCTACCTTGTAGTTCTGCTGAGTAGTCTCTCTGTGCTGGTGCTCAGCTATCT
80237      (2001)   CCTGCCTTCTTTCTTTGACATGCATGCATGTACTCTGTTATGTGATGGTAAATCTTAAGTAGTTCCTACCTTGTAGTTGTCTGCTGAGTAGTGTGTTTGCTGGTGCTCAGCTATCT
                                                                                                                  2200
ADV-IMI-R  (1828)   ATAGTGTCTTGTTGTTTGATGTCATGTACTCTGTATGTGACAGATAAATAAGGAAATAAGCATTGCTAATGCCAGTGGTTCTGTACGCCTC
80237      (2101)   ATAGTGTCTTGTTGTTTGATGTCATGTACTCTGTATGTGACAGATAAATAAGGAAATAAGCATTGCTAATGCCAGTGGTTCTGTACGCCTC
                    SbAHAS-R5                                                                            2274
ADV-IMI-R  (1928)   GAGGTCATGTAAGTGCCTTTTGCTACAGATAAATAAGGAAATAAGCATTGCTATGCAGTGGTTCTGTACGCCTC
80237      (2201)   GAGGTCATGTAAGTGCCTTTTGCTACAGATAAATAAGGAAATAAGCATTGCTATGCAGTGGTTCTGTACGCCTC
```

FIG. 2B

SEQUENCE LISTING

<160> NUMBER OF SEQ ID NOS: 34

<210> SEQ ID NO 1
<211> LENGTH: 2001
<212> TYPE: DNA
<213> ORGANISM: Sorghum bicolor

<400> SEQUENCE: 1

```
tcgaggctct tgagcgctgc ggcgtccgcg acgtcttcgc ctaccccggc ggcacgtcca      60
tggagatcca ccaggcactc acccgttccc ccgtcatcgc caaccacctc ttccgccacg     120
```

```
agcaagggga ggccttcgcc gcctctggct tcgcgcgctc ctcgggccgc gtcggcgtct    180
gcgtcgccac ctccggcccc ggcgccacca acctagtctc cgcgctcgcc gacgcgctgc    240
tcgactccgt ccccatggtc gccatcacgg acaggttcc gcggcgcatg attggcaccg     300
acgccttcca ggagacgccc atcgtcgagg tcaccgctc catcaccaaa cataactacc     360
tggtcctcga cgtcgacgac atccccgcg tcgtgcagga ggctttcttc ctcgcctcct     420
ccggtcgccc gggaccggtg cttgtcgaca tccccaagga catccagcag cagatggccg    480
tgccggtctg ggacacgccc atgagtctgc ctgggtacat tgcgcgcctt cccaagcctc    540
ctgcgactga attgcttgag caggtgctgc gtcttgttgg tgaatcaagg cgccctgttc    600
tttatgttgg tggtggctgc gcagcatctg gcgaggagtt gcgccgcttt gtggagatga    660
ctggaatccc agtcacaact actcttatgg gccttggcaa tttccctggc gacgacccac    720
tgtctctgcg catgcttggt atgcatggca cggtgtatgc aaattatgca gtggataagg    780
cggatctgtt gcttgcattt ggtgtgcggt ttgatgatcg tgtgacaggg aagattgagg    840
cttttgcaag cagggctaag attgtgcaca ttgatattga tcccgctgag attggcaaga    900
acaagcagcc acatgtgtcc atctgtgcag acgttaagct tgcttttgcag ggcatgaatg    960 ctcttctgga aggaagcaca tcaaagaaga gctttgactt tggctcatgg caagctgagt   1020
tggatcagca gaagagagag ttccccttg ggtataaaac ttttgatgac gagatccagc    1080
cacaatatgc tattcaggtt cttgatgagc tgacaaaagg ggaggccatc attgccacag   1140 gtgtgggca gcaccagatg tgggcggcac agtactacac ttacaagcgg ccaaggcagt    1200
ggttgtcttc agctggtctt ggggctatgg gatttggttt gccggctgct gctggcgctg    1260
ctgtggccaa cccaggtatc actgttgttg acatcgacgg agatggtagc ttcctcatga   1320
acattcagga gctagctatg atccgaattg agaacctccc agtgaaggtc tttgtgctaa   1380
acaaccagca cctggggatg gtggtgcagt gggaggacag gttctataag gccaatagag   1440
cacacacata cttgggaaac ccagagaatg aaagtgagat atatccagat tcgtgacaa    1500 ttgccaaagg gttcaacatt ccagcagtcc gtgtgacaaa gaagagcgaa gtccatgcag   1560
caatcaagaa gatgcttgag actccagggc catacctctt ggatataatc gtcccgcacc   1620
aggagcatgt gttgcctatg atccctagtg gtggggcttt caaggatatg atcctggatg   1680
gtgatggcag gactgtgtat tgatctaaat ttcagcatgc acatctccct gcctttctt    1740 gacatgcata tgagctggta caagggtgat gtgttattta tgtgatgttc tcctgtgttc   1800
tatctttttg taagccgtca gctatctata gtgtgcttgt ttgatgtact ctgttatggt   1860
aatcttaagt agtttcctac cttgtagtgg tgtagtctgt tgtttcgtgc tggcatatct   1920
gtcatcagag gtcatgtaag tgcctttgc tacagataaa taaggaaata agcattgcta    1980
tgcagtggtt ctgtacgcct c                                             2001
```

<210> SEQ ID NO 2
<211> LENGTH: 641
<212> TYPE: PRT
<213> ORGANISM: Sorghum bicolor

<400> SEQUENCE: 2

```
Met Ala Thr Thr Ala Ala Ala Ala Ala Ala Leu Ala Gly Ala Thr
1               5                   10                  15

Thr Ala Ala Pro Lys Arg Arg Arg Ala His Leu Leu Ala Ala Arg
            20                  25                  30
```

```
Arg Ala Leu Ala Ala Pro Ile Arg Cys Ser Ala Ala Pro Ala Thr
             35                  40                  45

Leu Thr Val Thr Ala Pro Ala Thr Pro Leu Arg Pro Trp Gly Pro
 50                  55                  60

Thr Asp Pro Arg Lys Gly Ala Asp Ile Leu Val Glu Ala Leu Glu Arg
 65                  70                  75                  80

Cys Gly Val Arg Asp Val Phe Ala Tyr Pro Gly Gly Thr Ser Met Glu
                 85                  90                  95

Ile His Gln Ala Leu Thr Arg Ser Pro Val Ile Ala Asn His Leu Phe
                100                 105                 110

Arg His Glu Gln Gly Glu Ala Phe Ala Ala Ser Gly Phe Ala Arg Ser
                115                 120                 125

Ser Gly Arg Val Gly Val Cys Val Ala Thr Ser Gly Pro Gly Ala Thr
         130                 135                 140

Asn Leu Val Ser Ala Leu Ala Asp Ala Leu Leu Asp Ser Val Pro Met
 145                 150                 155                 160

Val Ala Ile Thr Gly Gln Val Pro Arg Arg Met Ile Gly Thr Asp Ala
                 165                 170                 175

Phe Gln Glu Thr Pro Ile Val Glu Val Thr Arg Ser Ile Thr Lys His
                 180                 185                 190

Asn Tyr Leu Val Leu Asp Val Asp Asp Ile Pro Arg Val Val Gln Glu
                 195                 200                 205

Ala Phe Phe Leu Ala Ser Ser Gly Arg Pro Gly Pro Val Leu Val Asp
         210                 215                 220

Ile Pro Lys Asp Ile Gln Gln Gln Met Ala Val Pro Val Trp Asp Thr
225                 230                 235                 240

Pro Met Ser Leu Pro Gly Tyr Ile Ala Arg Leu Pro Lys Pro Pro Ala
                 245                 250                 255

Thr Glu Leu Leu Glu Gln Val Leu Arg Leu Val Gly Glu Ser Arg Arg
                 260                 265                 270

Pro Val Leu Tyr Val Gly Gly Gly Cys Ala Ala Ser Gly Glu Glu Leu
                 275                 280                 285

Arg Arg Phe Val Glu Met Thr Gly Ile Pro Val Thr Thr Thr Leu Met
 290                 295                 300

Gly Leu Gly Asn Phe Pro Gly Asp Asp Pro Leu Ser Leu Arg Met Leu
305                 310                 315                 320

Gly Met His Gly Thr Val Tyr Ala Asn Tyr Ala Val Asp Lys Ala Asp
                 325                 330                 335

Leu Leu Leu Ala Phe Gly Val Arg Phe Asp Asp Arg Val Thr Gly Lys
                 340                 345                 350

Ile Glu Ala Phe Ala Ser Arg Ala Lys Ile Val His Ile Asp Ile Asp
                 355                 360                 365

Pro Ala Glu Ile Gly Lys Asn Lys Gln Pro His Val Ser Ile Cys Ala
 370                 375                 380

Asp Val Lys Leu Ala Leu Gln Gly Met Asn Ala Leu Leu Glu Gly Ser
385                 390                 395                 400

Thr Ser Lys Lys Ser Phe Asp Phe Gly Ser Trp Gln Ala Glu Leu Asp
                 405                 410                 415

Gln Gln Lys Arg Glu Phe Pro Leu Gly Tyr Lys Thr Phe Asp Asp Glu
                 420                 425                 430

Ile Gln Pro Gln Tyr Ala Ile Gln Val Leu Asp Glu Leu Thr Lys Gly
                 435                 440                 445

Glu Ala Ile Ile Ala Thr Gly Val Gly Gln His Gln Met Trp Ala Ala
```

```
            450                 455                 460
Gln Tyr Tyr Thr Tyr Lys Arg Pro Arg Gln Trp Leu Ser Ser Ala Gly
465                 470                 475                 480

Leu Gly Ala Met Gly Phe Gly Leu Pro Ala Ala Gly Ala Ala Val
                485                 490                 495

Ala Asn Pro Gly Ile Thr Val Val Ile Asp Gly Asp Gly Ser Phe
            500                 505                 510

Leu Met Asn Ile Gln Glu Leu Ala Met Ile Arg Ile Glu Asn Leu Pro
                515                 520                 525

Val Lys Val Phe Val Leu Asn Asn Gln His Leu Gly Met Val Val Gln
            530                 535                 540

Trp Glu Asp Arg Phe Tyr Lys Ala Asn Arg Ala His Thr Tyr Leu Gly
545                 550                 555                 560

Asn Pro Glu Asn Glu Ser Glu Ile Tyr Pro Asp Phe Val Thr Ile Ala
                565                 570                 575

Lys Gly Phe Asn Ile Pro Ala Val Arg Val Thr Lys Lys Ser Glu Val
                580                 585                 590

His Ala Ala Ile Lys Lys Met Leu Glu Thr Pro Gly Pro Tyr Leu Leu
            595                 600                 605

Asp Ile Ile Val Pro His Gln Glu His Val Leu Pro Met Ile Pro Ser
            610                 615                 620

Gly Gly Ala Phe Lys Asp Met Ile Leu Asp Gly Asp Gly Arg Thr Val
625                 630                 635                 640

Tyr

<210> SEQ ID NO 3
<211> LENGTH: 641
<212> TYPE: PRT
<213> ORGANISM: Sorghum bicolor

<400> SEQUENCE: 3

Met Ala Thr Thr Ala Ala Ala Ala Ala Ala Leu Ala Gly Ala Thr
1               5                   10                  15

Thr Ala Ala Pro Lys Ala Arg Arg Ala His Leu Leu Ala Ala Arg
                20                  25                  30

Arg Ala Leu Ala Ala Pro Ile Arg Cys Ser Ala Ala Pro Pro Ala Thr
            35                  40                  45

Leu Thr Val Thr Ala Pro Pro Ala Thr Pro Leu Arg Pro Trp Gly Pro
50                  55                  60

Thr Asp Pro Arg Lys Gly Ala Asp Ile Leu Val Glu Ala Leu Glu Arg
65                  70                  75                  80

Cys Gly Val Arg Asp Val Phe Ala Tyr Pro Gly Gly Ala Ser Met Glu
                85                  90                  95

Ile His Gln Ala Leu Thr Arg Ser Pro Val Ile Ala Asn His Leu Phe
            100                 105                 110

Arg His Glu Gln Gly Glu Ala Phe Ala Ala Ser Gly Phe Ala Arg Ser
            115                 120                 125

Ser Gly Arg Val Gly Val Cys Val Ala Thr Ser Gly Pro Gly Ala Thr
130                 135                 140

Asn Leu Val Ser Ala Leu Ala Asp Ala Leu Leu Asp Ser Val Pro Met
145                 150                 155                 160

Val Ala Ile Thr Gly Gln Val Pro Arg Arg Met Ile Gly Thr Asp Ala
                165                 170                 175

Phe Gln Glu Thr Pro Ile Val Glu Val Thr Arg Ser Ile Thr Lys His
```

```
                180             185              190
Asn Tyr Leu Val Leu Asp Val Asp Ile Pro Arg Val Gln Glu
            195             200             205

Ala Phe Phe Leu Ala Ser Ser Gly Arg Pro Gly Pro Val Leu Val Asp
            210             215             220

Ile Pro Lys Asp Ile Gln Gln Met Ala Val Pro Val Trp Asp Thr
225             230             235             240

Pro Met Ser Leu Pro Gly Tyr Ile Ala Arg Leu Pro Lys Pro Pro Ala
                245             250             255

Thr Glu Leu Leu Glu Gln Val Leu Arg Leu Val Gly Glu Ser Arg Arg
                260             265             270

Pro Val Leu Tyr Val Gly Gly Cys Ala Ala Ser Gly Glu Glu Leu
            275             280             285

Arg Arg Phe Val Glu Met Thr Gly Ile Pro Val Thr Thr Thr Leu Met
290             295             300

Gly Leu Gly Asn Phe Pro Gly Asp Asp Pro Leu Ser Leu Arg Met Leu
305             310             315             320

Gly Met His Gly Thr Val Tyr Ala Asn Tyr Ala Val Asp Lys Ala Asp
                325             330             335

Leu Leu Leu Ala Phe Gly Val Arg Phe Asp Asp Arg Val Thr Gly Lys
                340             345             350

Ile Glu Ala Phe Ala Ser Arg Ala Lys Ile Val His Ile Asp Ile Asp
            355             360             365

Pro Ala Glu Ile Gly Lys Asn Lys Gln Pro His Val Ser Ile Cys Ala
            370             375             380

Asp Val Lys Leu Ala Leu Gln Gly Met Asn Ala Leu Leu Glu Gly Ser
385             390             395             400

Thr Ser Lys Lys Ser Phe Asp Phe Gly Ser Trp Gln Ala Glu Leu Asp
                405             410             415

Gln Gln Lys Arg Glu Phe Pro Leu Gly Tyr Lys Thr Phe Asp Asp Glu
            420             425             430

Ile Gln Pro Gln Tyr Ala Ile Gln Val Leu Asp Glu Leu Thr Lys Gly
            435             440             445

Glu Ala Ile Ile Ala Thr Gly Val Gly Gln His Gln Met Trp Ala Ala
            450             455             460

Gln Tyr Tyr Thr Tyr Lys Arg Pro Arg Gln Trp Leu Ser Ser Ala Gly
465             470             475             480

Leu Gly Ala Met Gly Phe Gly Leu Pro Ala Ala Ala Gly Ala Ala Val
                485             490             495

Ala Asn Pro Gly Ile Thr Val Val Asp Ile Asp Gly Asp Gly Ser Phe
                500             505             510

Leu Met Asn Ile Gln Glu Leu Ala Met Ile Arg Ile Glu Asn Leu Pro
            515             520             525

Val Lys Val Phe Val Leu Asn Asn Gln His Leu Gly Met Val Val Gln
            530             535             540

Trp Glu Asp Arg Phe Tyr Lys Ala Asn Arg Ala His Thr Tyr Leu Gly
545             550             555             560

Asn Pro Glu Asn Glu Ser Glu Ile Tyr Pro Asp Phe Val Thr Ile Ala
                565             570             575

Lys Gly Phe Asn Ile Pro Ala Val Arg Val Thr Lys Lys Ser Glu Val
                580             585             590

His Ala Ala Ile Lys Lys Met Leu Glu Thr Pro Gly Pro Tyr Leu Leu
            595             600             605
```

Asp Ile Ile Val Pro His Gln Glu His Val Leu Pro Met Ile Pro Ser
    610                 615                 620

Gly Gly Ala Phe Lys Asp Met Ile Leu Asp Gly Asp Gly Arg Thr Val
625                 630                 635                 640

Tyr

<210> SEQ ID NO 4
<211> LENGTH: 2274
<212> TYPE: DNA
<213> ORGANISM: Sorghum bicolor

<400> SEQUENCE: 4

| | | | | | |
|---|---|---|---|---|---|
| gtgcccccgc | cccaaaccct | cgcgccgcct | ccgagacagc | cgccgcaacc | atggccacca | 60 |
| ccgccgccgc | cgctgccgcc | gcgctagccg | gcgccactac | cgctgcgccc | aaggcgaggc | 120 |
| gccgggcgca | cctcctggcc | gcacggcgcg | ccctcgccgc | gcccatcagg | tgctcagcgg | 180 |
| cgccacccgc | cacgctgacg | gtgacggctc | ccccggccac | cccgctccgg | ccgtggggcc | 240 |
| ccaccgatcc | ccgcaagggc | gccgacatcc | tcgtcgaggc | tcttgagcgc | tgcggcgtcc | 300 |
| gcgacgtctt | cgcctacccc | ggcggcgcgt | ccatggagat | ccaccaggca | ctcacccgtt | 360 |
| cccccgtcat | cgccaaccac | ctcttccgcc | acgagcaagg | ggaggccttc | gccgcctctg | 420 |
| gcttcgcgcg | ctcctcgggc | cgcgtcgcg | tctgcgtcgc | cacctccggc | ccggcgcca | 480 |
| ccaacctagt | ctccgcgctc | gccgacgcgc | tgctcgactc | cgtccccatg | gtcgccatca | 540 |
| cgggacaggt | tccgcggcgc | atgattggca | ccgacgcctt | ccaggagacg | cccatcgtcg | 600 |
| aggtcacccg | ctccatcacc | aaacataact | acctggtcct | cgacgtcgac | gacatccccc | 660 |
| gcgtcgtgca | ggaggctttc | ttcctcgcct | cctccggtcg | cccgggaccg | gtgcttgtcg | 720 |
| acatccccaa | ggacatccag | cagcagatgg | ccgtgccggt | ctgggacacg | cccatgagtc | 780 |
| tgcctgggta | cattgcgcgc | cttcccaagc | tcctgcgac | tgaattgctt | gagcaggtgc | 840 |
| tgcgtcttgt | tggtgaatca | aggcgccctg | ttctttatgt | tggtggtggc | tgcgcagcat | 900 |
| ctggcgagga | gttgcgccgc | tttgtggaga | tgactggaat | cccagtcaca | actactctta | 960 |
| tgggccttgg | caatttccct | ggcgacgacc | cactgtctct | gcgcatgctt | ggtatgcatg | 1020 |
| gcacggtgta | tgcaaattat | gcagtggata | aggcggatct | gttgcttgca | tttggtgtgc | 1080 |
| ggtttgatga | tcgtgtgaca | gggaagattg | aggcttttgc | aagcagggct | aagattgtgc | 1140 |
| acattgatat | tgatcccgct | gagattggca | agaacaagca | gccacatgtg | tccatctgtg | 1200 |
| cagacgttaa | gcttgctttg | cagggcatga | atgctcttct | ggaaggaagc | acatcaaaga | 1260 |
| agagctttga | ctttggctca | tggcaagctg | agttggatca | gcagaagaga | gagttccccc | 1320 |
| ttgggtataa | aacttttgat | gacgagatcc | agccacaata | tgctattcag | gttcttgatg | 1380 |
| agctgacaaa | aggggaggcc | atcattgcca | caggtgttgg | gcagcaccag | atgtgggcgg | 1440 |
| cacagtacta | cacttacaag | cggccaaggc | agtggttgtc | ttcagctggt | cttgggggcta | 1500 |
| tgggatttgg | tttgccggct | gctgctggcg | ctgctgtggc | caacccaggt | atcactgttg | 1560 |
| ttgacatcga | cggagatggt | agcttcctca | tgaacattca | ggagctagct | atgatccgaa | 1620 |
| ttgagaacct | cccagtgaag | gtctttgtgc | taaacaacca | gcacctgggg | atggtggtgc | 1680 |
| agtgggagga | caggttctat | aaggccaata | gagcacacac | atacttggga | aacccagaga | 1740 |
| atgaaagtga | gatatatcca | gatttcgtga | caattgccaa | aggttcaac | attccagcag | 1800 |
| tccgtgtgac | aaagaagagc | gaagtccatg | cagcaatcaa | gaagatgctt | gagactccag | 1860 |

```
ggccatacct cttggatata atcgtcccgc accaggagca tgtgttgcct atgatcccta      1920
gtggtggggc tttcaaggat atgatcctgg atggtgatgg caggactgtg tattgatcta      1980
aatttcagca tgcacatctc cctgcctttc tttgacatgc atatgagctg gtacaagggt      2040
gatgtgttat ttatgtgatg ttctcctgtg ttctatcttt ttgtaagccg tcagctatct      2100
atagtgtgct tgtttgatgt actctgttat ggtaatctta agtagtttcc taccttgtag      2160
tggtgtagtc tgttgtttcg tgctggcata tctgtcatca gaggtcatgt aagtgccttt      2220
tgctacagat aaataaggaa ataagcattg ctatgcagtg gttctgtacg cctc            2274

<210> SEQ ID NO 5
<211> LENGTH: 18
<212> TYPE: DNA
<213> ORGANISM: Artificial sequence
<220> FEATURE:
<223> OTHER INFORMATION: Synthetic nucleic acid sequence

<400> SEQUENCE: 5
ctcgcgccgc ctccgaga                                                    18

<210> SEQ ID NO 6
<211> LENGTH: 18
<212> TYPE: DNA
<213> ORGANISM: Artificial sequence
<220> FEATURE:
<223> OTHER INFORMATION: Synthetic nucleic acid sequence

<400> SEQUENCE: 6
atgcgccgcg gaacctgt                                                    18

<210> SEQ ID NO 7
<211> LENGTH: 15
<212> TYPE: DNA
<213> ORGANISM: Artificial sequence
<220> FEATURE:
<223> OTHER INFORMATION: Synthetic nucleic acid sequence

<400> SEQUENCE: 7
tgctcgactc cgtcc                                                       15

<210> SEQ ID NO 8
<211> LENGTH: 16
<212> TYPE: DNA
<213> ORGANISM: Artificial sequence
<220> FEATURE:
<223> OTHER INFORMATION: Synthetic nucleic acid sequence

<400> SEQUENCE: 8
catcaaaccg cacacc                                                      16

<210> SEQ ID NO 9
<211> LENGTH: 15
<212> TYPE: DNA
<213> ORGANISM: Artificial sequence
<220> FEATURE:
<223> OTHER INFORMATION: Synthetic nucleic acid sequence

<400> SEQUENCE: 9
atgcatggca cggtg                                                       15

<210> SEQ ID NO 10
<211> LENGTH: 15
<212> TYPE: DNA
<213> ORGANISM: Artificial sequence
```

```
<220> FEATURE:
<223> OTHER INFORMATION: Synthetic nucleic acid sequence

<400> SEQUENCE: 10
cagcagccgg caaac                                                      15

<210> SEQ ID NO 11
<211> LENGTH: 15
<212> TYPE: DNA
<213> ORGANISM: Artificial sequence
<220> FEATURE:
<223> OTHER INFORMATION: Synthetic nucleic acid sequence

<400> SEQUENCE: 11
cacaggtgtt gggca                                                      15

<210> SEQ ID NO 12
<211> LENGTH: 16
<212> TYPE: DNA
<213> ORGANISM: Artificial sequence
<220> FEATURE:
<223> OTHER INFORMATION: Synthetic nucleic acid sequence

<400> SEQUENCE: 12
cttgaaagcc ccacca                                                     16

<210> SEQ ID NO 13
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 13
ggagctagct atgatccgaa                                                 20

<210> SEQ ID NO 14
<211> LENGTH: 18
<212> TYPE: DNA
<213> ORGANISM: Artificial sequence
<220> FEATURE:
<223> OTHER INFORMATION: Synthetic nucleic acid sequence

<400> SEQUENCE: 14
cagaaccact gcatagca                                                   18

<210> SEQ ID NO 15
<211> LENGTH: 19
<212> TYPE: DNA
<213> ORGANISM: Artificial sequence
<220> FEATURE:
<223> OTHER INFORMATION: Synthetic nucleic acid sequence

<400> SEQUENCE: 15
tcgaggctct tgagcgctg                                                  19

<210> SEQ ID NO 16
<211> LENGTH: 18
<212> TYPE: DNA
<213> ORGANISM: Artificial sequence
<220> FEATURE:
<223> OTHER INFORMATION: Synthetic nucleic acid sequence

<400> SEQUENCE: 16
atgcgccgcg gaacctgt                                                   18
```

<210> SEQ ID NO 17
<211> LENGTH: 15
<212> TYPE: DNA
<213> ORGANISM: Artificial sequence
<220> FEATURE:
<223> OTHER INFORMATION: Synthetic nucleic acid sequence

<400> SEQUENCE: 17
ccgcgacgtc ttcgc                                                    15

<210> SEQ ID NO 18
<211> LENGTH: 18
<212> TYPE: DNA
<213> ORGANISM: Artificial sequence
<220> FEATURE:
<223> OTHER INFORMATION: Synthetic nucleic acid sequence

<400> SEQUENCE: 18
tgcctggtgg atctccat                                                 18

<210> SEQ ID NO 19
<211> LENGTH: 15
<212> TYPE: DNA
<213> ORGANISM: Artificial sequence
<220> FEATURE:
<223> OTHER INFORMATION: Synthetic nucleic acid sequence

<400> SEQUENCE: 19
taccccggcg gcacg                                                    15

<210> SEQ ID NO 20
<211> LENGTH: 15
<212> TYPE: DNA
<213> ORGANISM: Artificial sequence
<220> FEATURE:
<223> OTHER INFORMATION: Synthetic nucleic acid sequence

<400> SEQUENCE: 20
taccccggcg gcgcg                                                    15

<210> SEQ ID NO 21
<211> LENGTH: 16
<212> TYPE: DNA
<213> ORGANISM: Artificial sequence
<220> FEATURE:
<223> OTHER INFORMATION: Synthetic nucleic acid sequence

<400> SEQUENCE: 21
agatctggcg gcaacg                                                   16

<210> SEQ ID NO 22
<211> LENGTH: 18
<212> TYPE: DNA
<213> ORGANISM: Artificial sequence
<220> FEATURE:
<223> OTHER INFORMATION: Synthetic nucleic acid sequence

<400> SEQUENCE: 22
agtcacccat cgatcatc                                                 18

<210> SEQ ID NO 23
<211> LENGTH: 15
<212> TYPE: DNA
<213> ORGANISM: Artificial sequence
<220> FEATURE:
<223> OTHER INFORMATION: Synthetic nucleic acid sequence

<400> SEQUENCE: 23
gccggttgtg acttg                                                        15

<210> SEQ ID NO 24
<211> LENGTH: 18
<212> TYPE: DNA
<213> ORGANISM: Artificial sequence
<220> FEATURE:
<223> OTHER INFORMATION: Synthetic nucleic acid sequence

<400> SEQUENCE: 24
ttaaagcgat gggtgtag                                                     18

<210> SEQ ID NO 25
<211> LENGTH: 19
<212> TYPE: DNA
<213> ORGANISM: Artificial sequence
<220> FEATURE:
<223> OTHER INFORMATION: Synthetic nucleic acid sequence

<400> SEQUENCE: 25
cgattggaca taagtgttc                                                    19

<210> SEQ ID NO 26
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 26
tataaacatc agcagaggtg                                                   20

<210> SEQ ID NO 27
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 27
tcagtgatac agccgtccag                                                   20

<210> SEQ ID NO 28
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 28
atgcataaac cacggctgtc                                                   20

<210> SEQ ID NO 29
<211> LENGTH: 17
<212> TYPE: DNA
<213> ORGANISM: Artificial sequence
<220> FEATURE:
<223> OTHER INFORMATION: Synthetic nucleic acid sequence

<400> SEQUENCE: 29
gtgccgcttt gctcgca                                                      17

<210> SEQ ID NO 30

```
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 30
tgctatgttg tttgcttctc ccttctc                                              27

<210> SEQ ID NO 31
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 31
gtgaagcatc ccaaccctta                                                      20

<210> SEQ ID NO 32
<211> LENGTH: 19
<212> TYPE: DNA
<213> ORGANISM: Artificial sequence
<220> FEATURE:
<223> OTHER INFORMATION: Synthetic nucleic acid sequence

<400> SEQUENCE: 32
gcctttttcc gtcttcgag                                                       19

<210> SEQ ID NO 33
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 33
tcgggtatta gccctttgtg                                                      20

<210> SEQ ID NO 34
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 34
acacctcctc ttggtggatg                                                      20
```

SORGHUM PLANTS HAVING A MUTANT POLYNUCLEOTIDE ENCODING THE LARGE SUBUNIT OF MUTATED ACETOHYDROXYACID SYNTHASE PROTEIN AND INCREASED RESISTANCE TO HERBICIDES

BACKGROUND

Sorghum (*Sorghum* spp.) is a plant genus comprising approximately 20 species of grasses. It is native to tropical and subtropical regions of East Africa and it is grown in every continent for grain for human and animal consumption, being also used as fodder, and for manufacturing alcoholic beverages. As it is gluten-free, sorghum is suitable for individuals suffering from celiac disease.

Sorghum is more tolerant to drought and excess soil moisture content than most cereals. It is capable of growing properly under varied soil and weather conditions. Likewise, it responds favorably to irrigation, requiring a minimum of 250 mm during its life cycle, with an optimum irrigation ranging from 400-550 mm.

The soil must have an appropriate moisture content at the time of planting in order to achieve a rapid and homogeneous emergence and thereby a good crop implantation. The greatest demand of water starts 30 days after emergence and continues until grains are filled, the most critical stages being those of panicle formation and flowering, as water deficiency at this time will result in decreasing yields.

Furthermore, sorghum has the ability of remaining dormant during periods of drought and resumes growth under favorable periods, although these stress situations may affect performance.

Sorghum requires high temperatures for normal development, and consequently it is more sensitive to low temperatures than other crops. A soil temperature of not less than 18° C. is required for germination; and actual active growth of the plant is not achieved until a temperature of 15° C. is reached, the optimum temperature being of about 32° C.

Acetohydroxyacid synthase (AHAS) is the first enzyme which catalyzes the synthesis of branched amino acids valine, leucine and isoleucine. AHAS is the target of some herbicides such as sulfonylureas, imidazolinones, triazolopyrimidines and pyrimidyloxybenzoates. The two former herbicide families are widely used in modern agriculture due to their low toxicity and high efficacy against weeds.

The imidazolinone family of herbicides comprises imazethapyr, imazaquin, and imazapyr.

Some sulfonylureas present in the market are: metsulfuron-methyl, chlorosulfuron, nicosulfuron, cinosulfuron, imidasulfuron, halosulfuron, rimsulfuron, trisulfuron-methyl, and tribenuron-methyl.

However, there are plants which are resistant to herbicides of the imidazolinone and/or sulfonylurea families; for example, species such as *Zea mays, Arabidopsis thaliana, Brassica napus, Glycine max, Nicotiana tabacum,* and *Oryza sativa* (Sebastian et al., (1989) *Crop Sci.,* 29: 1403-1408; Swanson et al., 1989 *Theor. Appl. Genet.* 78: 525-530; Newhouse et al., (1991) *Theor. Appl. Genet.,* 83: 65-70; Sathasivan et al., (1991) *Plant Physiol.,* 97: 1044-1050; Mourand et al., (1993) *J. Heredity* 84: 91-96; U.S. Pat. No. 5,545,822). A point mutation has been described in sunflower, in the large subunit of AHAS, which confers resistance to herbicides of the type of imidazolinones (WO 2007/0118920).

Plants resistant to herbicides of the imidazolinone or sulfonylurea type have also been detected. These plants have acquired resistance naturally and have been used for crossbreeding, resulting in herbicide-resistant varieties. From the analysis of resistant plants, a point mutation was determined in the AHAS protein of sunflower resulting in the substitution of the amino acid Ala by Val (White et al., (2003) *Weed Sci.,* 51: 845-853).

In addition, U.S. Pat. Nos. 4,761,373; 5,331,107; 5,304,732; 6,211,438; 6,211,439; and 6,222,100 disclose plants resistant to imidazolinone herbicides. All these patents generally describe the use of an altered AHAS gene to elicit herbicide resistance in plants, and specifically disclose certain imidazolinone resistant corn lines. U.S. Pat. Nos. 5,731,180 and 5,767,361 discuss an isolated gene having a single amino acid substitution in a wild-type monocot AHAS amino acid sequence that results in imidazolinone-specific resistance.

Patent documents WO 2006/007373 and WO 2006/060634 disclose mutations conferring resistance to herbicides of the imidazolinone type in wheat plants.

The publication "Amino acids conferring herbicide resistance in tobacco acetohydroxyacid synthase" describes different point mutations in AHAS that confer herbicide resistance (*GM Crops* 1: 2, 62-67; Feb. 16, 2010).

Patent document US 20100115663 refers to herbicide-resistant sorghum plants achieved by altering acetyl CoA carboxylase genes. Also disclosed are sorghum plants resistant to the herbicide dinitroaniline (US 20100205686) and sorghum plants resistant to the herbicide acetolactate synthase (WO2008/073800).

SUMMARY OF THE INVENTION

The sorghum plants of the present invention show improved resistance to herbicides, for example herbicides targeting the AHAS enzyme, i.a., imidazolinones and sulfonylureas, as compared to wild-type sorghum plants. In particular, the sorghum plant (*Sorghum bicolor*) of the present invention comprises in its genome at least one polynucleotide. Said polynucleotide encodes a large subunit of AHAS having an alanine to tyrosine substitution at position 93 of the large subunit of sorghum AHAS or an equivalent position, wherein said plant has increased resistance to one or more herbicides, such as herbicides selected from the group of imidazolinones, as compared to wild-type sorghum plants. The sorghum plant may comprise in its genome, one, two, three or more copies of a polynucleotide encoding a mutated large subunit of sorghum AHAS or a sorghum AHAS polypeptide of the invention. In this context, the sorghum plant may be tolerant to any herbicide capable of inhibiting AHAS enzyme activity, i.e., the sorghum plant may be tolerant to herbicides of the imidazolinone type, such as, without limitation, imazethapyr, imazapir, and imazapic or to herbicides of the group of sulfonylureas, such as, without limitation, chlorosulfuron, metsulfuron methyl, sulfometuron methyl, chlorimuron ethyl, thiofensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfuron, fluzasulfuron, imazosulfuron, pyrazosulfuron ethyl, and halosulfuron.

In a preferred embodiment, the sorghum plant of the invention which is resistant to herbicides belonging to the group of imidazolinones or sulfonylureas is the sorghum line designated VT11-11331-BK which seeds were deposited with the NCIMB collection under Access No. NCIMB 41870, on Oct. 12, 2011, under the terms of the Budapest Treaty. The mutated VT11-11331-BK plant, parts thereof and its seeds, comprise in their genome the mutated AHAS gene comprising a polynucleotide having the nucleotide sequence set forth in SEQ ID No. 1 encoding the polypeptide or AHAS large subunit having the sequence set forth in SEQ ID No. 2. The amino acid sequence of SEQ ID No. 2 corresponding to the large subunit of AHAS differs in one amino acid from the wild-type amino acid sequence of the large subunit of sorghum AHAS (SEQ ID No. 3), said difference comprising an alanine to tyrosine substitution at position 93 of the large subunit of sorghum AHAS, or equivalent positions.

The herbicide-tolerant sorghum plant germoplasm of the invention is useful for introducing the tolerance trait by introgression into other sorghum varieties. The sorghum plants of the present invention include progeny and seeds of plants comprising a polynucleotide, where said polynucleotide encodes an AHAS large subunit and has an alanine to tyrosine substitution at position 93 of said large subunit of sorghum AHAS or at an equivalent position, wherein said plant shows an increased resistance to one or more imidazolinone and/or sulfonylurea herbicides as compared to wild-type sorghum plants.

In a preferred embodiment, the herbicide-resistant sorghum plant comprises the resistance traits of NCIMB 41870, and may be a plant as described in NCIMB 41870, a progeny of an NCIMB 41870 plant, a mutant of an NCIMB 41870 plant, and a progeny of an NCIMB 41870 mutant. The plant may be transgenic or non-transgenic and belong to any plant species suitable for agronomical use, or for other uses, such as ornamentals.

Further provided is a sorghum seed, comprising in its genome at least one polynucleotide, wherein said polynucleotide encodes a polypeptide having an alanine to tyrosine substitution at position 93 of the sorghum AHAS protein large subunit. The seed germinates and produces a plant having increased resistance to one or more herbicides of the imidazolinone group as compared to wild-type sorghum plants. In a preferred embodiment said seed is the seed deposited as NCIMB 41870.

Further provided is a method for identifying a plant resistant to herbicides from the group of imidazolinones or sulfonylureas, comprising:
a) supplying a nucleic acid sample from a sorghum plant;
b) amplifying a region corresponding to an AHAS gene from a sorghum plant present in said nucleic acid sample;
c) identifying a sorghum plant resistant to herbicides of the imidazolinone group based on the presence of at least one mutation in said amplified nucleic acid sample that confers resistance to imidazolinone herbicides. In a preferred embodiment, plants comprising at least one mutation in AHAS such as the mutation in NCIMB 41870 are selected, where said at least one mutation in the AHAS gene encodes a polypeptide or large subunit of AHAS comprising a Ala93Tyr substitution as compared to the wild-type sorghum AHAS amino acid sequence. The plant may be a monocot or a dicot. Preferably the plant is a plant of agronomic interest, such as sorghum, rice, corn, soybean, wheat, oat, barley, rye, flax, cotton, sugarcane, sunflower, or the like. The method of identification may employ a specific point mutation SNP marker.

The present invention provides a method for controlling weeds in the near proximity of agronomic plants, for example sorghum plants, where said sorghum plants are resistant to herbicides, such as herbicides from the group of imidazolinones and/or sulfonylureas. In a preferred embodiment, the herbicide is an imidazolinone. The imidazolinone herbicide may be imazethapyr, imazapic, or imazapyr. The plant may exhibit resistance traits such as NCIMB 41870, and it may be a derivative, mutant, or progeny plant thereof.

The present invention provides a polypeptide comprising, without limitation, one or more of the following nucleotide sequences:
the sequence set forth in SEQ ID No. 1,
a nucleotide sequence encoding the polypeptide of SEQ ID No. 2,
a nucleotide sequence encoding a polypeptide having at least 95% sequence identity to the amino acid sequence of SEQ ID No. 2, wherein the polypeptide exhibits herbicide-resistant AHAS activity;
a nucleotide sequence having at least 85% identity to the nucleotide sequence set forth in SEQ ID No. 1, wherein the nucleotide sequence encodes a polypeptide comprising a large subunit of AHAS and exhibits herbicide-resistant AHAS activity,
or complementary sequences thereof.
Preferably the polynucleotide encodes a polypeptide of the large unit of AHAS comprising an Ala93Tyr substitution.

The present invention also provides an expression cassette comprising at least one polynucleotide having the following nucleotide sequence: SEQ ID No. 1, a nucleotide sequence encoding the polypeptide set forth in SEQ ID No. 2, a nucleotide sequence encoding a polypeptide having at least 95% sequence identity to amino acid sequence SEQ ID No. 2, wherein the polypeptide exhibits herbicide-resistant AHAS activity; a nucleotide sequence having at least 85% identity to the nucleotide sequence set forth in SEQ ID No. 1, wherein the nucleotide sequence encodes a polypeptide comprising a large subunit of AHAS and exhibits herbicide-resistant AHAS activity, or complementary sequences thereof. Preferably, the polynucleotide encodes a polypeptide of the large unit of AHAS comprising an Ala93Tyr substitution; said sequences being operably linked to a nucleotide sequence for conducting expression, for example one or more promoters, enhancers or other known regulatory sequences. The promoter may be a promoter for expression in plants, plant tissues, chloroplasts, animal, bacterial, fungal or yeast cells.

The present invention provides a transformation vector comprising at least one polynucleotide having one of the following nucleotide sequences: a) the nucleotide sequence set forth in SEQ ID No. 1, b) a nucleotide sequence encoding the polypeptide set forth in SEQ ID No. 2, c) a nucleotide sequence encoding a polypeptide having at least 95% sequence identity to the amino acid sequence of SEQ ID No.:2, where the polypeptide exhibits herbicide-resistant AHAS activity, d) a nucleotide sequence having at least 85% identity to the nucleotide sequence set forth in SEQ ID No.:1, where the nucleotide sequence encodes a polypeptide comprising a large subunit of AHAS and exhibits herbicide-resistant AHAS activity; further comprising operably linked sequences driving the expression of the nucleotide sequence and selectable markers. The vector may be used for transforming bacteria, fungi, yeasts, plant cells or animal cells, being adapted for each particular case.

The present invention provides a transformed plant comprising, integrated in its genome, at least one promoter operably linked to a polynucleotide selected from: a) the nucleotide sequence set forth in SEQ ID No. 1, b) a nucleotide sequence encoding the polypeptide set forth in SEQ ID No. 2; c) a nucleotide sequence encoding a polypeptide having at least 95% sequence identity to amino acid sequence SEQ ID No. 2, where the polypeptide exhibits herbicide-resistant AHAS activity; d) a nucleotide sequence having at least 85% identity to the nucleotide sequence set forth in SEQ ID No. 1, where the nucleotide sequence encodes a polypeptide comprising a large subunit of AHAS and having herbicide-resistant AHAS activity; e) a nucleotide sequence fully complementary to one of nucleotide sequences a) to (d), where the vector further comprises a selectable gene and at least one promoter operably linked to a nucleotide sequence that drives the expression of said nucleotide sequence. The promoter is a promoter driving polypeptide expression in plants, for example in plant tissues or chloroplasts. The transformed plants may be monocots, for example sorghum, corn, rice, or wheat; or dicots, for example sunflower, Arabidopsis, tobacco or oilseed rape. The transformed plant is resistant to herbicides (imidazolinones and sulfonylureas) over the same wild-type plant when equal amounts of said herbicides are applied to both.

The invention also provides a method for obtaining a herbicide-resistant plant or a plant having increased resistance to a herbicide, said method comprising the steps of i) transforming a plant cell with an expression cassette comprising a polynucleotide ii) regenerating the plant cell to obtain a herbicide-resistant plant, said polynucleotide having at least one of the following nucleotide sequences: a) the nucleotide sequence set forth in SEQ ID No. 1, b) a nucleotide sequence encoding the polypeptide set forth in SEQ ID No. 2, c) a nucleotide sequence encoding a polypeptide having at least 95% sequence identity to amino acid sequence SEQ ID No. 2, where the polypeptide exhibits herbicide-resistant AHAS activity, d) a nucleotide sequence having at least 85% identity to the nucleotide sequence set forth in SEQ ID No. 1, where the nucleotide sequence encodes a polypeptide comprising a 1a large subunit of AHAS and has herbicide-resistant AHAS activity and e) a nucleotide sequence fully complementary to one of the nucleotide sequences a) to (d). The DNA expression cassette comprises at least one promoter for driving the expression of the polypeptide in plants, for example in plant tissues or chloroplasts. The transformed plants may be monocots, for example sorghum, corn, rice or wheat; or dicots, for example sunflower, Arabidopsis, tobacco, soybean, or oilseed rape. The transformed plant is resistant to herbicides (imidazolinones and sulfonylureas) as compared to the wild-type plant when equal amounts of said herbicides are applied to both. The plant comprises the large subunit of AHAS resistant to herbicides.

DESCRIPTION OF THE DRAWINGS

Figure 2A:
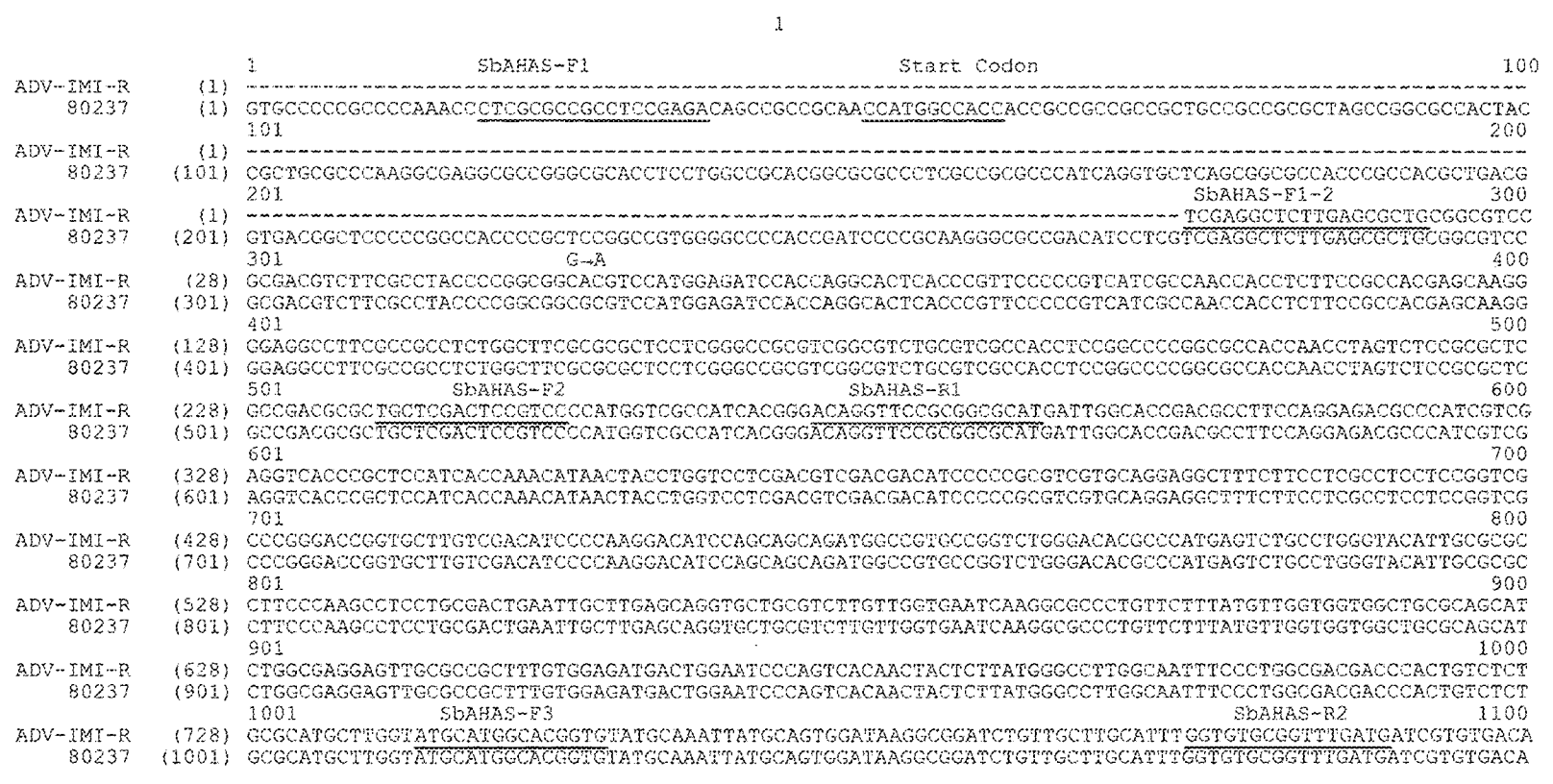

FIGS. 2A-2B show the alignment of mutant ADV-IMI-R AHAS nucleotide sequences and those of the original endogamic sorghum line 80237 or wild-type line. G to A substitution of nucleotides is indicated at position +277, which distinguishes both sequences. The different primers used for amplifying overlapping amplicon sequences are underlined.

DETAILED DESCRIPTION OF THE INVENTION

In order to obtain herbicide-tolerant plants, endogamic sorghum (Sorghum bicolor) line 80237 plants were treated with an aqueous solution of ethyl methanesulfonate (EMS). Treated seeds were planted and left for open pollination. Two hundred and seventy three M1 plants were selected and two seeds of each plant were planted in a nursery, thereby obtaining a total of 546 M2 plants. Pollen from one plant of each pair was collected and used for pollinating the other plant of the pair. M3 seeds obtained from each of the 273 pollinated M2 plants were harvested. A total of 273 furrows were planted with the M3 progeny. Fifty plants from each M3 furrow were sprayed with 100 ml L a.i./ha of imazethapyr. Sixty eight plants from the furrows showed normal growth and absence of symptoms after the treatment with herbicide and were considered as resistant to the herbicide and identified as VT09-9754. The genealogy of the resistant plants from the furrows was identified and they were designated 80237EMS2-192 (hereinafter referred to as ADV-IMI-R). Herbicide-tolerant M7 mutant plants and seeds selected from the original ADV-IMI-R mutant (designated VT11-11331-BK) were obtained and deposited with the NCIMB collection with Access No. NCIMB 41870, under the terms of the Budapest Treaty, on Oct. 12, 2011.

The present invention is not limited to sorghum plants mutated with EMS. Within the scope of the present invention are sorghum plants obtained by other mutation methods, for example methods such as radiation and chemical mutagens. Herbicide-resistant mutant plants can also be obtained by means of a process of selective pressure on cells cultured with a herbicide and selection of resistant cells to generate a herbicide-resistant plant. Details of mutation and breeding methods can be found in "Principles of Cultivar Development" Fehr, 1993, Macmillan Publishing Company, the disclosure of which is included herein by reference.

Subsequently, the effect to herbicide spraying on mutant imidazolinone-resistant plants ADV-IMI-R (original mutation) was compared to the response of endogamic sorghum line 80237 (Advanta proprietary elite line). To that end, plants were treated on the field with three herbicides belonging to the imidazolinone family: imazethapyr, imazapir, and imazapic. Four different rates were assayed: 1×, 2×, 3×, and 4× for each of the herbicides. The recommended field application rate (1×) for each herbicide is shown in Table 1.

TABLE 1

Recommended field application rate for each herbicide

| Herbicide | Trade name | Recommended rate (1X) |
|---|---|---|
| Imazethapyr | Pivot ® (BASF) | 100 ml a.i./ha |
| Imazapyr | Clearsol DF ®(BASF) | 80 g a.i./ha |
| Imazapic | Cadre ® (BASF) | 50.4 g a.i./ha |

Figure 1A:
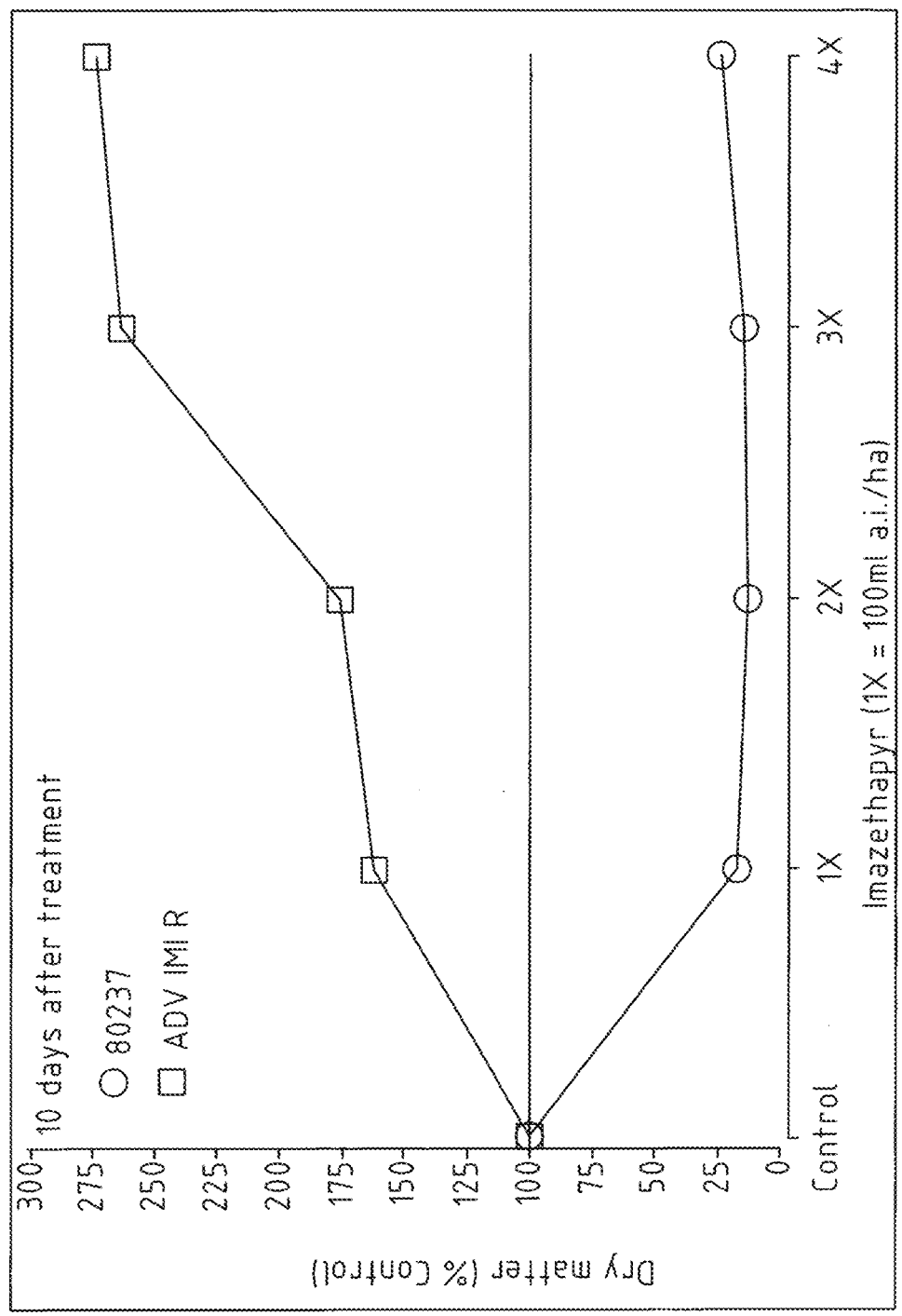
FIGS. 1A-1C show dose-response curves of the imidazolinone-resistant mutant sorghum line (ADV-IMI-R) and the original endogamic sorghum line 80237 or wild-type line. Assayed herbicides were: imazethapyr, imazapyr and imazapic at rates of 0 (control), 1×, 2×, 3×, and 4×. Herbicidal effect was measured as a percentage of dry matter (DM) of aerial tissues as compared to an untreated control; each value being the average of three assays.
Figure 1B:
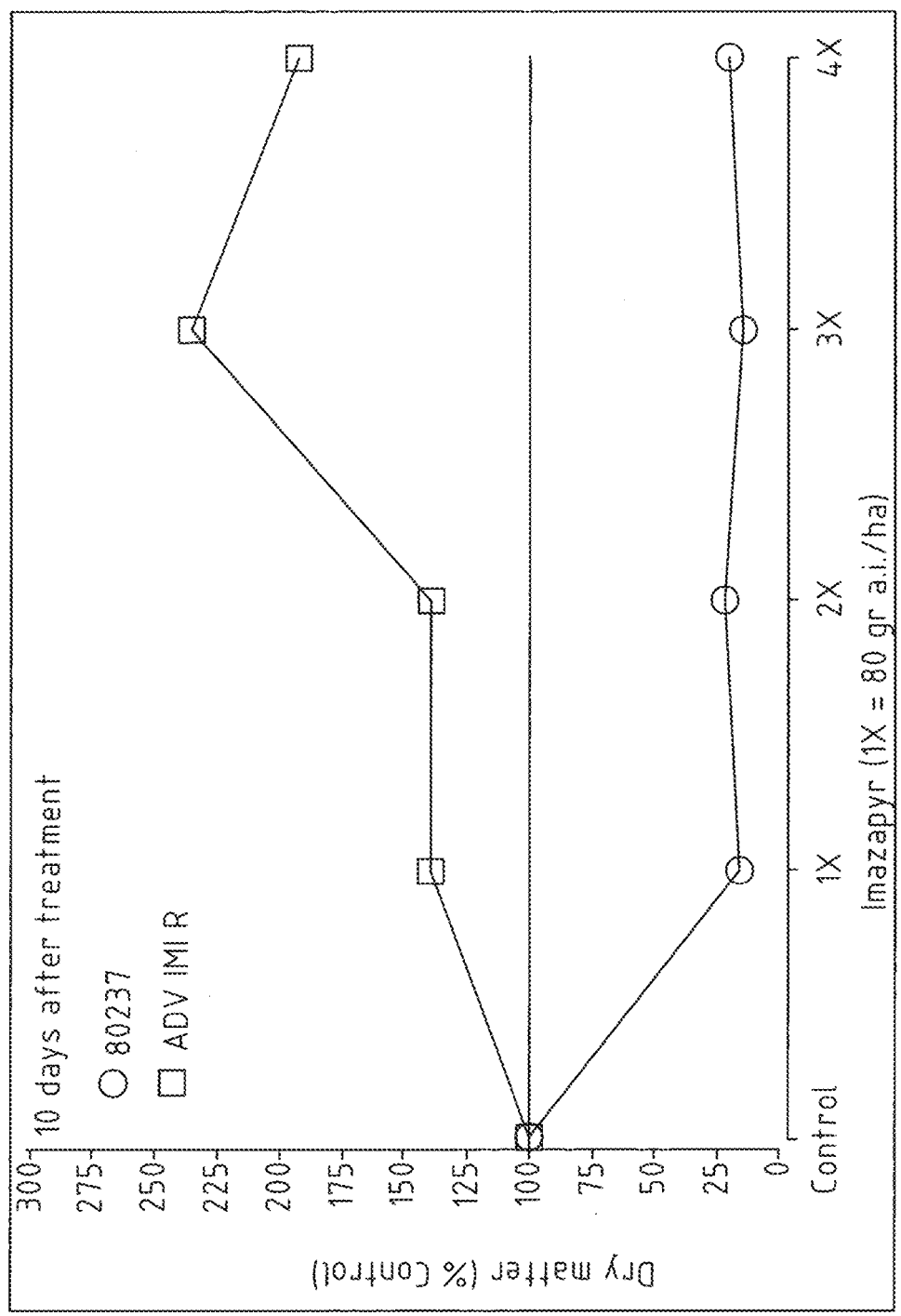
Figure 1C:
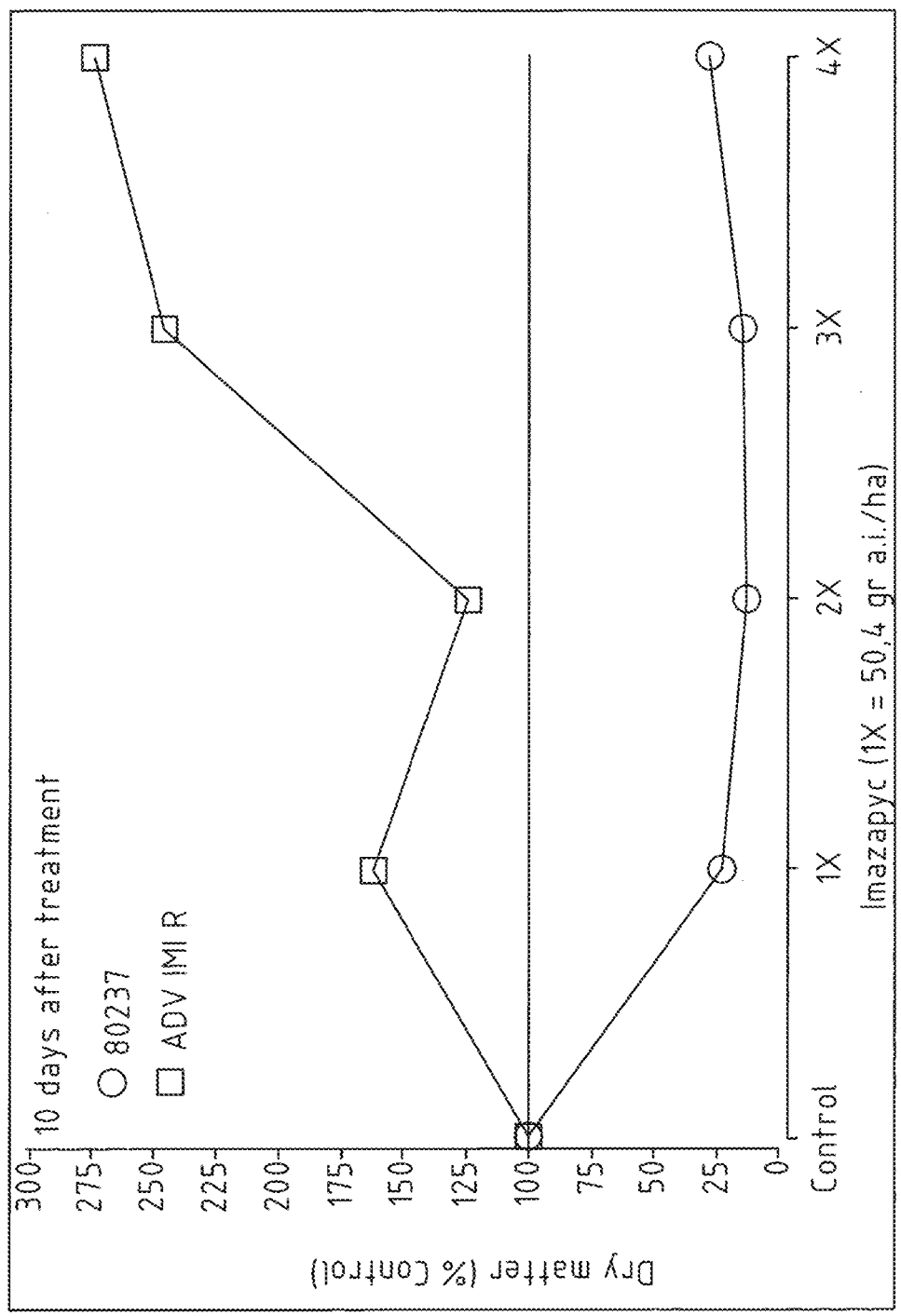

Ten days after spraying, all plants were assayed for dry matter (DM) in aerial tissues. The results are shown in FIGS. 1A-1C.

The response of the ADV-IMI-R mutant of the invention was compared to that of endogamic line 80237. Table 2 shows the effect of different rates of imazethapyr, imazapyr, and imazapic expressed as a percentage of dry matter as compared to the untreated control (DM % Control). The disclosed values are the average of three experiments.

TABLE 2

| | | DM % Control | |
|---|---|---|---|
| Herbicide | Rate | 80237 | ADV-IMI-R |
| Untreated control | 0X | 100 | 100 |
| Imazethapyr | 1X | 17 | 162 |
| | 2X | 12 | 175 |
| | 3X | 14 | 263 |
| | 4X | 23 | 273 |
| Imazapyr | 1X | 14 | 139 |
| | 2X | 21 | 140 |
| | 3X | 14 | 235 |
| | 4X | 19 | 191 |
| Imazapic | 1X | 22 | 161 |
| | 2X | 13 | 123 |
| | 3X | 15 | 244 |
| | 4X | 28 | 272 |

These results show that the ADV-IMI-R mutant of the invention is resistant to the three tested herbicides of the imidazolinone group, even at a rate of 4×. On the contrary, the original endogamic line 80237 is clearly sensitive to all the herbicides, even when the recommended rate (1×) is applied.

As can be seen, the herbicide-resistant sorghum plant of the present invention is resistant to herbicides of the imidazolinone group, such as, imazethapyr, imazapic, or imazapyr.

The imidazolinone-resistant sorghum plants may be sprayed with amounts which are 4 times the recommended amounts of use of any of the group of known imidazolinone herbicides. The resistant plant may have, for example, the resistance traits as observed in plants from NCIMB 41870 seeds, or it may be a plant derived therefrom, a progeny, or other plants comprising in their genome at least one polynucleotide encoding a polypeptide having an alanine to tyrosine substitution at position 93 of the sorghum AHAS protein or at an equivalent position, said plant having increased resistance to one or more herbicides from the imidazolinone group as compared to wild-type sorghum plants.

Furthermore, those of ordinary skill will recognize that such amino acid positions can vary depending on whether amino acids are added or removed, e.g., from the N-terminal end of an amino acid sequence. By "equivalent position" it is intended to mean a position that is within the same conserved region as the exemplified amino acid position.

In the present invention the terms "tolerant" to a herbicide and "resistant" to a herbicide have the same meaning and an equivalent scope when used in relation to herbicides such as imidazolinones or sulfonylureas.

The present invention provides plants, plant cells, plant tissues showing resistance to effective amounts of herbicides. By "effective amounts" is meant amounts of herbicide capable of inhibiting the growth of wild-type plants, plant cells or tissues but which do not produce severe effects on resistant plants, plant cells or plant tissues. An effective amount of a herbicide is the recommended amount for eliminating weeds. A wild-type plant, cell or tissue is one that does not exhibit herbicide resistance traits, for example a herbicide belonging to the group of imidazolinones or sulfonylureas. The term "plant" encompasses a plant in any stage, or plant parts, where said plant parts may be seeds, leaves, flowers, stems, tissues or organs, well known to a skilled botanist.

In order to detect the mutation, the mutated sorghum AHAS gene of the invention which encodes a polypeptide having acetohydroxyacid synthase activity was sequenced, wherein said AHAS polypeptide or large subunit is herbicide-resistant.

A comparison of the AHAS gene DNA sequence from mutated plants with the AHAS gene DNA sequences from wild-type sorghum plants identified a point mutation by which a G nucleotide at nucleotide position +277 changes into A, which distinguishes the original sorghum 80237 line (wild-type) from the ADV-IMI-R mutant of the invention. When AHAS amino acid sequences from mutant and wild-type lines were deduced it was observed that the nucleotide substitution (GCG by ACG of SEQ ID No. 1) encoded a mutated polypeptide at codon 93 and produced an alanine to tyrosine (Ala93Tyr) substitution in the polypeptide (SEQ ID No. 2) exhibiting acetohydroxyacid synthase activity and corresponds to the large subunit of sorghum AHAS protein of the mutated ADV-IMI-R line.

Within the scope of the present invention are plants, plant parts, seeds, progeny thereof, transgenic plants or the like comprising a polynucleotide encoding a polypeptide having an alanine-to-tyrosine (Ala93Tyr) substitution at position 93 of said polypeptide or at an equivalent position of another AHAS enzyme belonging to different species.

Within the scope of the present invention is a polynucleotide or a polypeptide having a sequence identity of at least 85%, 95%, or 98%. Sequence identity percent is determined by alignment of two amino acid sequences or two nucleotide sequences. Alignment percentage between two sequences may be calculated, for example, using the following formula:

(amount of identical positions/total amount of overlapping positions)×100

Alignment percentage between two sequences is determined using different mathematical algorithms, for example, the algorithms included in the NBLAST and XBLAST programs of Altschul et al., (1990) *J. Mol. Biol.* 215: 403. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. Alignment may also be performed by manual inspection.

The present invention comprises polynucleotides and proteins conferring herbicide resistance. It is understood that when reference is made to a herbicide-resistant polynucleotide it means a polynucleotide encoding a herbicide-resistant AHAS protein. Herbicide-resistant AHAS proteins may be natural or mutant and they confer resistance to herbicides belonging to the group of imidazolinones or sulfonylureas.

Inheritance of resistance to imidazolinones, for example imazethapyr, was assessed in a segregating F2 sorghum population generated by crossing an imazethapyr susceptible line with the ADV-IMI-R mutant. The F2 plants thus obtained were sprayed with imazethapyr (Pivot®, BASF) at a rate of 3×, 20 days in stage V6 after emergence and phenotypic symptoms were assessed 10 days after treatment. The results are provided in Table 3.

TABLE 3

Distribution of plants based on phenotypic rating

| Phenotype | Phenotypic rating | Amount of F2 progeny |
|---|---|---|
| No damage | 1 | 50 |
| Chlorotic | 2 | 84 |
| Death | 3 | 43 |
| | | 177 |

The results show that the F2 plant population could be classified based on visual symptoms according to a phenotype scoring that allowed for grouping individuals into three phenotypic categories: plants with no damage, chlorotic plants and dead plants.

Sequencing showed that the herbicide-tolerant sorghum mutant of the invention had a point mutation in the polypeptide having acetohydroxyacid synthase activity or the large subunit of AHAS protein. The nucleotide sequence set forth in SEQ ID No. 1 shows that nucleotide G is changed to A at nucleotide position +277 (corresponding to codon 93) which distinguishes the sorghum original endogamic line 80237 (susceptible to herbicides) from the induced ADV-IMI-R mutant of the invention. This molecular marker was designated SNP-SbAHAS.

Figure 3:
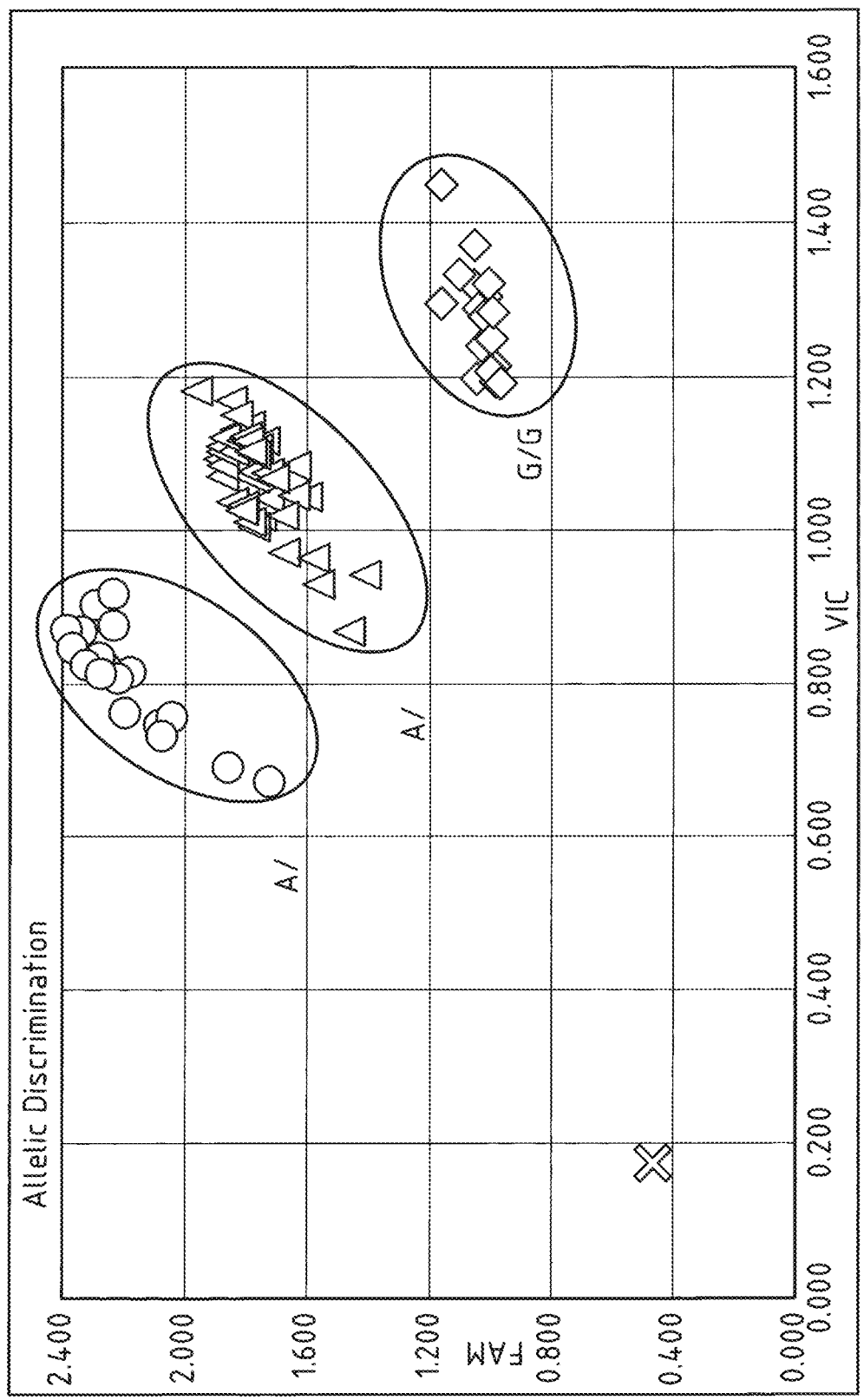
FIG. 3 shows genotyping assays for a SNP G/A at codon 93 of sorghum AHAS gene. The specific SNP-SbAHAS marker was analyzed in the genotype of 177 F2 progeny plants from ADV-IMI-R×F2 90523. Three clusters were clearly defined and identified as dots (●) corresponding to homozygous plants for the mutant allele (A/A), triangles (▲) corresponding to heterozygous plants (A/G) and diamonds (♦) for homozygous plants of the wild-type allele (G/G).

In order to determine the usefulness of the SNP-SbAHAS marker for detecting potentially herbicide-resistant plants, plant parts or seeds, 177 plants from an F2 population generated by crossing the herbicide-resistant ADV-IMI-R mutant (selection VT09-9754-48-6-BK) with the herbicide-susceptible endogamic line 90523 (herein designated population ADV-IMI-R×90523 F2) were tested. FIG. 3 shows as an example the allelic discrimination of some plants from the F2 population. The two tested controls were grouped in the expected clusters (ADV-IMI-R mutant and wild-type 90523, homozygous resistant and homozygous susceptible, respectively). These data confirm that the molecular marker SNP-SbAHAS is useful for distinguishing the three allelic combinations at nucleotide position +277 of the polynucleotide encoding a polypeptide having acetohydroxyacid synthase activity or the large subunit of sorghum AHAS protein.

Those skilled in the art may, in view of the disclosure of the SNP-SbAHAS marker and its use, identify herbicide-resistant plants, for example to herbicides belonging to the group of imidazolinones and/or sulfonylureas, e.g., imazethapyr, imazapic, or the like. The identification method may be, in addition to the method described herein, any other known method, see for example ASA (Soleimani et al., (2003) Plant Mol Biol Rep 21: 281-288), PAMSA (Daudet et al., (2007) Plant Mol Biol Rep 25: 1-9), SSCP (Germano and Klein (1999) Theor Appl Genet 99: 37-49) or TagMan® (Jones et al., (2008) Pest Management Science 64: 12-15).

The correlation between resistance phenotypes and the number of mutant alleles was analyzed using the SNP-SbAHAS marker. To that end, chlorosis and death phenotypes of individual plants from the F2 progeny (ADV-IMI-R×90523) were studied after spraying with imazethapyr. Concomitantly, the genotype of the SNP-SbAHAS marker was studied. The results are shown in Table 4. The correlation between the molecular marker SNP-SbAHAS and resistance to imazethapyr (measured as a rating of phenotypes) was determined using the Chi-square Independence test. The test resulted in a probability $p=1.948e^{-46}$ indicative of a highly significant correlation between the induced mutation in the AHAS gene (genotyped using the specific SNP-SbAHAS marker) and resistance to imazethapyr in accordance with phenotype and genotype co-segregation.

TABLE 4

Phenotypes and ratings of resistance to Imazethapyr for the ADV-IMI-R × 90523 F2 progeny based on the analysis of SNP-SbAHAS. A/A homozygous AHAS mutant; A/G heterozygous; G/G wild-type homozygous

| Phenotype | Phenotypic score | Amount of F2 individuals for each genotype | | |
|---|---|---|---|---|
| | | A/A | A/G | G/G |
| No damage | 1 | 37 | 13 | 50 |
| Chlorotic | 2 | 1 | 83 | 84 |
| Death | 3 | | | 43 | 43 |
| | | 38 | 96 | 43 | 177 |

Figure 4:
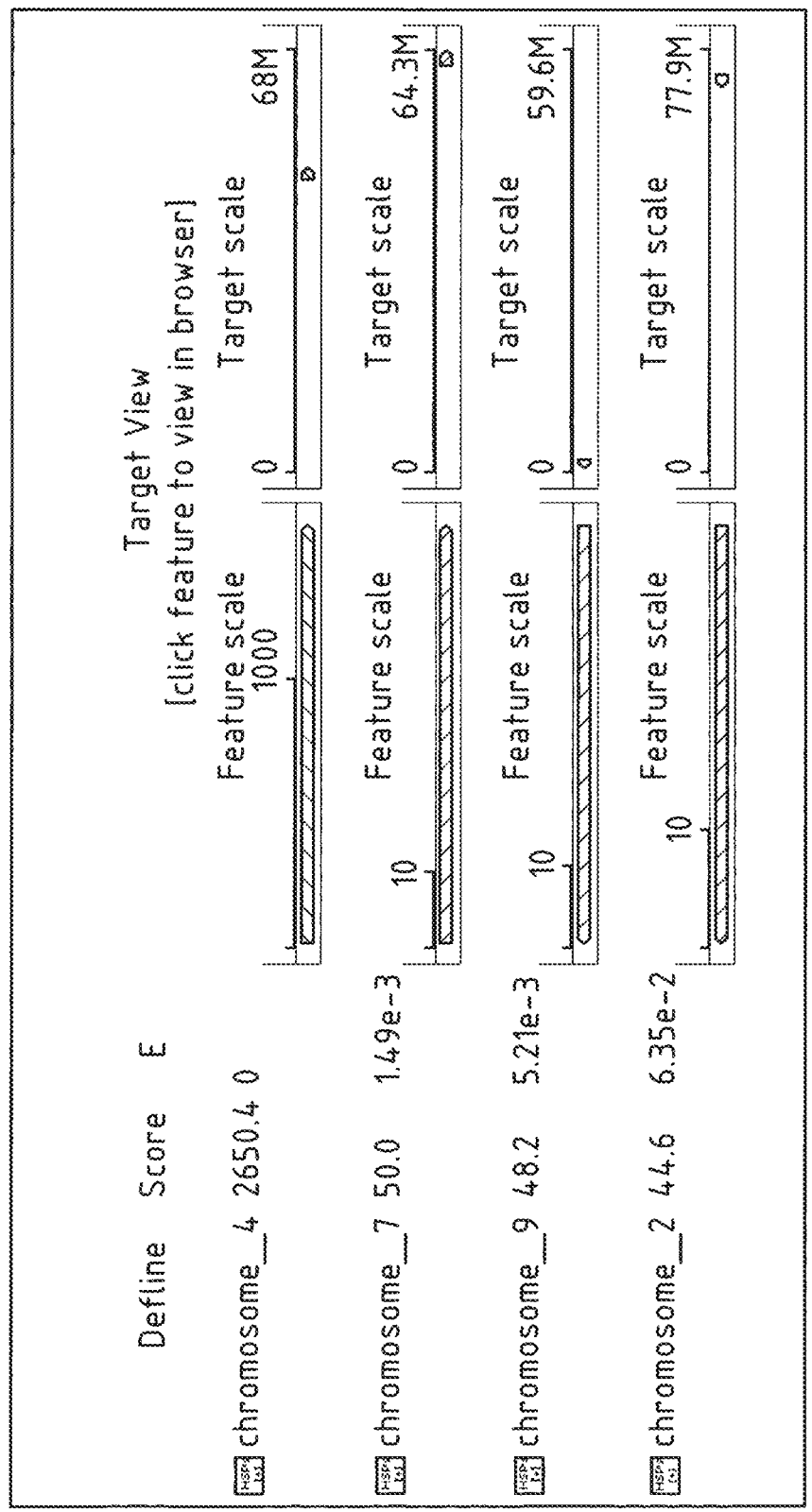
FIG. 4 shows the results obtained by matching the nucleotide sequence of the sorghum AHAS gene (Access No. GM663363.1) with sorghum genomic sequences (Sorghum bicolor) deposited with the Phytozome nucleotide sequence database (http://www.phytozome.net/search.php). This matching shows that the AHAS GM663363.1 sequence exhibits a highly significant homology (value e=0) to an AHAS sequence located at chromosome 4 of sorghum genome indicating that the gene of interest is present in this linkage group.

Further, genetic mapping of herbicide-resistance and the specific SNP-SbAHAS marker was carried out. Based on the sorghum AHAS sequence disclosed in GenBank (Access No. GM663363.1, SEQ ID No. 4), a BLAST analysis was carried out to match Sorghum bicolor DNA sequence with the Phytozome database (http://www.phytozome.net/search.php). The results shown in FIG. 4 indicate that the AHAS sequence associated with resistance to herbicides belonging to the group of imidazolinones is located in chromosome 4 of Sorghum bicolor genome. A fingerprinting (genotyped) procedure based on this information was carried out for the mutated ADV-IMI-R line of the invention and endogamic 90253 line using various SSRs-type DNA molecular markers. Seven polymorphic SSRs located in chromosome 4 were selected for genotyping (Mace, E S et al., *A consensus genetic map of sorghum that integrates multiple component maps and high-throughput Diversity Array Technology (DArT) markers*, BMC Plant Biology, 2009, 9: 13; Srinivas, G et al., *Exploration and mapping of microsatellite markers from subtracted drought stress ESTs in Sorghum bicolor* (L.), Moench. Theor. Appl. Genet. 2009, 118: 703-717; Ramu, P et al., *In silico mapping of important*

*genes and markers available in the public domain for efficient sorghum breeding*, Mol Breeding 2010, 26: 409-418; http://www.lbk.ars.

usda.gov/psgd/sorghum/2009SorghumSEAMs_LBKARS.xls)

Figure 5:
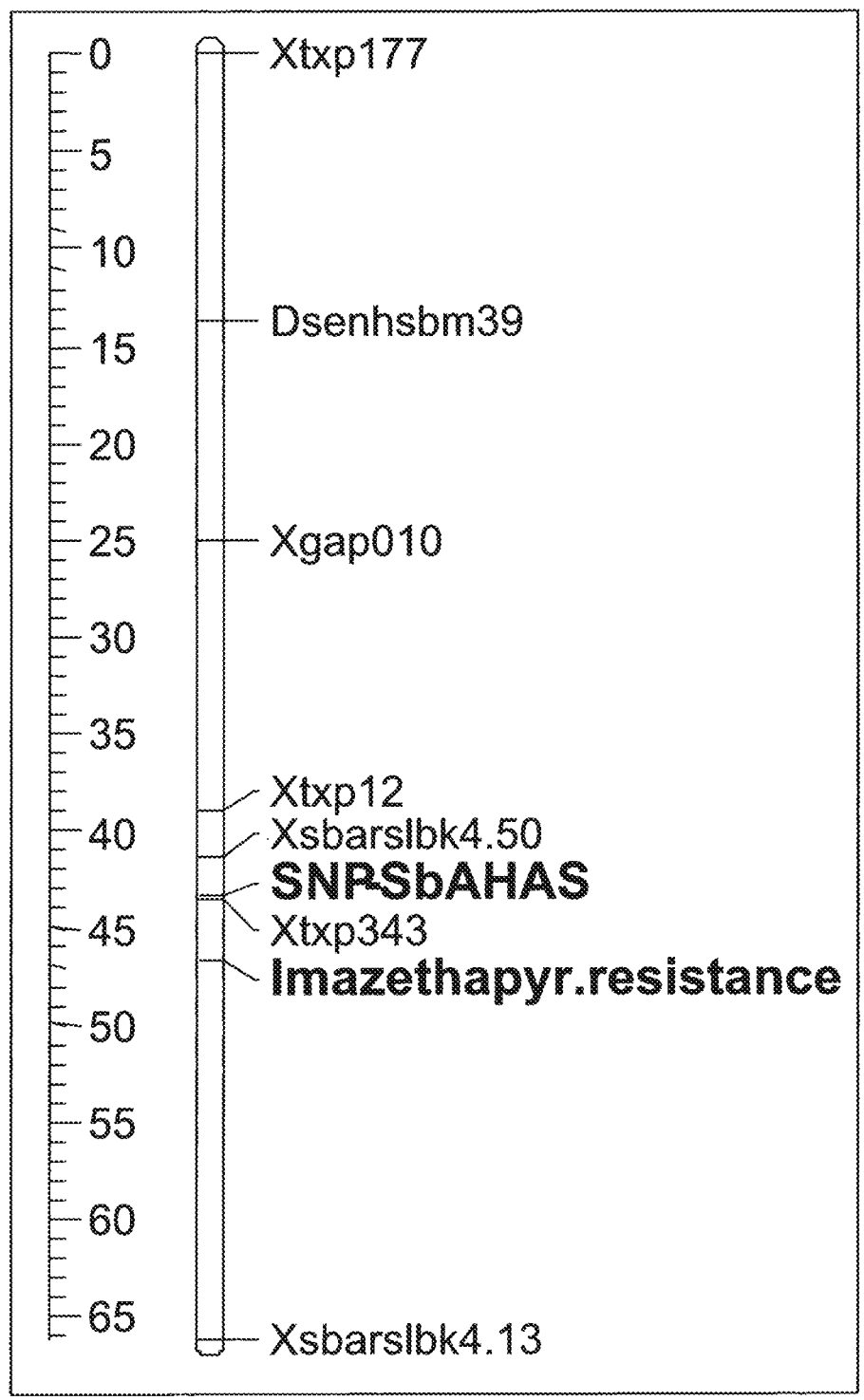
FIG. 5 shows a linkage map of S. bicolor chromosome 4. Distances between adjacent markers are given in centimorgans (cM). The chromosomic position of SNP-SbAHAS and of resistance to imazethapyr with reference to the 7 SSRs in chromosome 4 of the genotype of the 177 F2 plants is indicated. The map was built using JoinMap software, using default parameters of LOD=3 and a maximum Kosambi distance of 50 cM.

With the results of this procedure it was possible to genetically map both the SNP-SbAHAS marker and the resistant phenotype, showing that the resistance to imidazolinones and the specific SNP-SbAHAS marker were located in chromosome 4 flanked by the previously identified SSRs in chromosome 4 of Sorghum bicolor (FIG. 5).

The polynucleotide of the invention (SEQ ID No. 1) may be introduced in plants for obtaining transgenic plants. There are different methods for introducing a polynucleotide in plants, particularly in plants of agronomic interest, e.g., corn, soybean, sorghum, wheat, sugarcane, flax, sunflower or other plants; vegetables, trees, or ornamental plants. Methods for introducing polynucleotides to obtain transgenic plants are well-known in the art, and recombinant methods may also be used.

There are different methods for plant transformation, for example using vectors (An, G. et al., (1986) *Plant Pysiol.*, 81: 301-305; Fry, J., et al., (1987) *Plant Cell Rep.*, 6: 321-325; Block, M. (1988) *Theor. Appl Genet.*, 76: 767-774; Hinchee, et al., (1990) *Stadler. Genet. Symp.*, 203212.203-212; Barcelo, et al., (1994) *Plant J.*, 5: 583-592; Becker, et al., (1994) *Plant J.*, 5: 299-307; Borkowska et al., (1994) *Acta Physiol Plant.*, 16: 225-230; Christou, et al., (1992) *Trends Biotechnol.*, 10: 239-246; D'Halluin, et al., (1992) *Bio/Technol.*, 10: 309-314; Dhir, et al., (1992) *Plant Physiol.*, 99: 81-88; Casas et al., (1993) *Proc. Nat. Acad Sci. USA* 90: 11212-11216; Dong, J. A. and Mchughen, A. (1993) *Plant Sci.*, 91: 139-148; Golovkin, et al., (1993) *Plant Sci.*, 90: 41-52; *Guo Chin Sci., Bull.*, 38: 2072-2078; Asano, et al., (1994) *Plant Cell Rep.*, 13; Christou, P. (1994) *Agro. Food. Ind. Hi Tech.*, 5: 17-27; Eapen et al., (1994) *Plant Cell Rep.*, 13: 582-586; Hartman, et al., (1994) *Bio-Technology* 12: 919923; Christou, P. (1993) *In Vitro Cell. Dev. Biol.-Plant;* 29P: 119-124; Davies, et al., (1993) *Plant Cell Rep.*, 12: 180-183; Ritala, et al., (1994) *Plant. Mol. Biol.* 24:317-325; and Wan, Y. C. and Lemaux, P. G. (1994) *Plant Physiol.*, 104:3748).

Some methods for transforming plants and genetic engineering techniques are described in Sambrook, et al., (1989) *Molecular cloning*, A laboratory manual, Cold Spring Harbor Press, Plainview, N.Y.; Ausubel F M, et al., *Current Protocols in Molecular Biology*, John Wiley & Sons, New York, N.Y.

The vector may also be introduced using ballistic particle acceleration techniques such as described in U.S. Pat. No. 4,945,050 and Casas el. al., *Proc. Natl. Sci., USA,* 90: 11212, 1993

Plants transformed, for example, with the polynucleotide of the invention express herbicide-resistant AHAS proteins and exhibit resistance traits to herbicides such as imidazolinones and/or sulfonylureas. By "herbicide-resistant AHAS proteins" are meant proteins exhibiting an AHAS activity which is higher than that of wild-type AHAS activity when in the presence of a herbicide interfering with AHAS activity at concentrations at which the herbicide interferes with AHAS activity of the wild-type AHAS protein.

The polynucleotide sequence of the invention may be included in an expression cassette for expressing the resistant AHAS protein in a plant of interest, for example of agronomic interest. The cassette comprises a regulatory sequence operably linked, e.g., to at least one promoter. Promoters are well known in the art, and may be, e.g., constitutive, inducible, tissue-specific, chloroplast-specific promoters, all of them being functional in plants. The cassette further comprises transcriptional termination sequences known in the art. The cassette may comprise various regulatory sequences in order to improve expression efficiency of the herbicide-resistant AHAS polynucleotide, for example enhancers such as introns, viral sequences or the like; or may comprise other polynucleotide sequences of interest different from the polynucleotide of the invention, bound or not to said polynucleotide; or leader sequences.

Promoters include, but are not limited to, constitutive, inducible, tissue- or organelle-specific promoters, such as the 35S promoter, a wound- or chemical-inducible promoter, a heat shock promoter, a tetracycline-inducible promoter or the like (Chao et. al. 1999, *Plant Physiol.*, 120: 979; U.S. Pat. Nos. 5,187,267, 5,057,422.

Also known by those skilled in the art are suitable transcription terminators which may be of use in plants, see, e.g., Odell, et al., 1985, *Nature* 313: 810; Sanfacon, et. al., *Genes Dev.*, 5: 141, 1990; Munroe, et al., 1990 *Gene* 91: 151; Rosenberg et al., 1987, *Gene* 56: 125; Joshi, et al., *Nucleic Acid Res.*, 15: 9627, 1987.

"Operably linked" is intended to refer to a functional linkage between a promoter and a second sequence. The promoter sequence initiates and mediates transcription of the DNA sequence corresponding to the second sequence. The term "operably linked" means that the nucleic acid sequences being linked are contiguous and, where necessary to join two protein coding regions, contiguous and in the same reading frame. The cassette may be a multiple expression cassettes.

The polynucleotide of the invention may be attached to other polynucleotides in the form of a fusion of polynucleotides or separately. The other polynucleotide(s) may encode, e.g., herbicide-resistant, insect-resistant or other plant parts which are well-known by those skilled in the art.

To improve expression in plants, the polynucleotide of the invention may be modified, for example by including plant-preferred codons, deleting sequences such as introns or deleterious sequences. Also, within the scope of the present invention is a polynucleotide encoding the resistant AHAS polypeptide of the invention which has been mutated, and exhibits, e.g., deletions or insertions or other mutations different from the one described herein. By "mutated polynucleotide" is meant a polynucleotide having permanent changes in its nucleotide sequence.

The polynucleotide of the invention may be altered by substitutions, deletions, truncations, and insertions. Methods for such manipulations are generally known in the art. Methods for mutagenesis and nucleotide sequence alterations are well known in the art (Kunkel (1985) *Proc. Natl. Acad. Sci., USA* 82: 488-492; Kunkel et al., (1987) *Methods in Enzymol.*, 154: 367-382; Walker and Gaastra, eds., (1983) *Techniques in Molecular Biology* (MacMillan Publishing Company, New York) and the references cited therein. Amino acid substitutions that do not affect biological activity of the protein of interest may be found in Dayhoff et al., (1978) *Atlas of Protein Sequence and Structure* (Natl. Biomed. Res. Found., Washington, D.C.), herein incorporated by reference.

The DNA comprising the AHAS polynucleotide of the invention may be introduced in different plants as part of a vector. The choice of a suitable vector depends on the method intended to be used for the transformation and the plant to be transformed. Those skilled in the art are well aware of different vectors, e.g., Ti and/or Ri. T-DNA is also used as flanking regions for integrating Ti or Ri vectors (WO 84/02913, Herrera-Estrella et al., 1983, *Nature* 303: 209; Horsch et al., 1984, *Science* 223: 496; Fraley et. al., 1983, *Proc. Natl. Acad. Sci, USA* 80: 4803.

The vector may comprise an expression cassette and other nucleotide sequences, for example selectable markers such as markers conferring resistance to antibiotics or herbicides and sequences for driving the expression of polynucleotide(s) of interest in plants, e.g., the AHAS large subunit polypeptide of SEQ ID No. 2.

A vector comprising a polynucleotide encoding the resistant AHAS polypeptide of the invention may be useful for obtaining a transgenic plant which is resistant to herbicides of the type of imidazolinones and sulfonylureas. The transformed plants may be any type of plants such as dicots and monocots, among which are, without limitation, plants of agronomic interest such as sorghum (*Sorghum bicolor, Sorghum vulgare*), maize (*Zea mays*), *Brassica* sp. (e.g., *B. napus, B. rapa, B. juncea*), alfalfa (*Medicago sativa*), rice (*Oryza sativa*), rye (*Secale cereale*), millet (*Pennisetum glaucum*), (*Panicum miliaceum*), (*Setaria italica*), (*Eleusine coracana*), sunflower (*Helianthus annuus*), wheat (*Triticum aestivum, T. Turgidum* ssp. *durum*), soybean (*Glycine max*), tobacco (*Nicotiana tabacum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), safflower (*Carthamus tinctorius*), pineapple (*Ananas comosus*), citrus trees (*Citrus* spp.), cocoa (*Theobroma cacao*), tea (*Camellia sinensis*), banana (*Musa* spp.), avocado (*Persea americana*), olive (*Olea europaea*), cashew (*Anacardium occidentale*), almond (*Prunus amygdalus*), sugar beets (*Beta vulgaris*), potato (*Solanum tuberosum*), sugarcane (*Saccharum* spp.), vegetables, ornamentals, and trees. Preferably, the plant of the present invention is *sorghum*.

The invention is further described by the following numbered paragraphs:

1. A sorghum plant comprising in its genome at least one polynucleotide, wherein said polynucleotide encodes a polypeptide having an alanine to tyrosine substitution at position 93 of the large subunit of sorghum AHAS protein, said plant having increased resistance to one or more herbicides as compared to wild-type sorghum plants.

2. The sorghum plant according to paragraph 1, wherein the herbicide is selected from the group consisting of imidazolinone and sulfonylurea 3. The sorghum plant according to paragraph 2, wherein the imidazolinone herbicide is selected from the group consisting of imazethapyr, imazapir, and imazapic.

4. The sorghum plant according to paragraph 1, wherein at least one polynucleotide comprises SEQ ID No. 1.

5. The sorghum plant according to paragraph 1, wherein the encoded polypeptide comprises SEQ ID No. 2.

6. The sorghum plant according to paragraph 1, comprising a mutation in the AHAS gene as set forth in NCIMB 41870.

7. The sorghum plant according to paragraph 1, wherein said sorghum plant comprises increased resistance traits to one or more herbicides of the imidazolinone group as the resistance set forth for NCIMB 41870.

8. The sorghum plant according to any of paragraphs 6 and 7, wherein said sorghum plant with increased resistance to one or more herbicides is useful for introducing the resistance trait by introgression into another sorghum plant.

9. The sorghum plant according to paragraph 1, wherein said plant is transgenic.

10. The sorghum plant according to paragraph 1, wherein said plant is non-transgenic.

11. A herbicide-resistant sorghum plant comprising the resistance traits of NCIMB 41870, wherein the sorghum plant is selected from the group consisting of a plant such as NCIMB 41870, a progeny of the NCIMB 41870 plant, an NCIMB 41870 mutant plant and a progeny of the NCIMB 41870 mutant.

12. The sorghum plant according to paragraph 11, wherein the herbicide belongs to the group of imidazolinones.

13. The sorghum plant according to paragraph 11, wherein said plant is transgenic.

14. The sorghum plant according to paragraph 11, wherein said plant is non-transgenic.

15. A sorghum seed, comprising in its genome at least one polynucleotide, wherein said polynucleotide encodes a polypeptide having an alanine to tyrosine substitution at position 93 of the large subunit of sorghum AHAS protein.

16. The seed according to paragraph 15, wherein said seed generates a plant having increased resistance to one or more herbicides from the group of imidazolinones as compared to wild-type sorghum plants.

17. The seed according to paragraph 15, wherein said seed comprises a mutation in the AHAS gene as shown in the deposited seed NCIMB 41870.

18. A seed of a plant according to any of paragraph 1 to 10.

19. A seed of the plant according to any of paragraphs 11 to 14.

20. A method for identifying a herbicide-resistant plant, comprising:
   a) providing a nucleic acid sample from a sorghum plant;
   b) amplifying a region corresponding to the AHAS gene present in said nucleic acid sample from a sorghum plant;
   c) identifying a herbicide-resistant plant based on the presence of at least one mutation in the amplified nucleic acid sample, where said mutation confers resistance to herbicides from the imidazolinone group.

21. The method according to paragraph 20, wherein the nucleic acid sample comprises at least one mutation such as the mutation present in NCIMB 41870.

22. The method according to paragraph 20, wherein said at least one mutation comprises an Ala93Tyr substitution in the encoded polypeptide, wherein said polypeptide has acetohydroxyacid synthase activity.

23. The method according to paragraph 20, wherein the nucleic acid sample comprises SEQ ID No. 1.

24. The method according to paragraph 22, wherein the polypeptide comprises SEQ ID No. 2.

25. The method according to paragraph 20 wherein the plant is a monocot.

26. The method according to paragraph 20 wherein the plant is a dicot.

27. The method according to paragraph 20 wherein the plant is a transgenic plant.

28. The method according to paragraph 20, wherein the plant is a non-transgenic plant.

29. The method according to paragraph 20, wherein the herbicide is selected from the group of imidazolinones and sulfonylureas.

30. A method of weed control in close proximity to crop plants, comprising applying an effective amount of a herbicide from the group of imidazolinones or sulfonylurea to weed and crop plants.

31. The method according to paragraph 30, wherein the imidazolinone herbicide is selected from the group consisting of imazethapyr, imazapic, and imazapyr.

32. The method according to paragraph 30, wherein the crop plant is selected from the group consisting of
    a) a sorghum plant comprising in its genome at least one polynucleotide, wherein said polynucleotide encodes a polypeptide having an alanine to tyrosine substitution at position 93 of the sorghum AHAS protein, wherein said plant has increased resistance to one or more herbicides from the group of imidazolinone or sulfonylurea as compared to wild-type sorghum plants;
    b) a sorghum plant comprising a mutation in the AHAS gene such as in NCIMB 41870;
    c) a sorghum plant comprising increased resistance traits to one or more herbicides from the group of imidazolinone or sulfonylurea such as the resistance shown by NCIMB 41870.
    d) a plant, progeny, derivative or mutant of sorghum plants a) to c).
33. A polynucleotide, comprising a nucleotide sequence selected from the group consisting of:
    a) the nucleotide sequence set forth in SEQ ID No. 1,
    b) a nucleotide sequence encoding the polypeptide set forth in SEQ ID No. 2;
    c) a nucleotide sequence encoding a polypeptide having at least 95% sequence identity to amino acid sequence SEQ ID No. 2, wherein the polypeptide has herbicide-resistant AHAS activity;
    d) a nucleotide sequence having at least 85% identity to the nucleotide sequence set forth in SEQ ID No. 1, wherein the nucleotide sequence encodes a polypeptide comprising a large subunit of AHAS and exhibits herbicide-resistant AHAS activity;
    e) a nucleotide sequence fully complementary to one of nucleotide sequences a) to (d).
34. The polynucleotide according to paragraph 33, wherein said polynucleotide encodes a polypeptide comprising an Ala93Tyr substitution in the large subunit of AHAS.
35. An expression cassette comprising, operably linked thereto, the nucleotide sequence of paragraph 33.
36. The expression cassette according to paragraph 35, further comprising at least one promoter that drives the expression of the polynucleotide.
37. The expression cassette according to paragraph 36, wherein the promoter is selected from the group comprising promoters for expression in plants, bacteria, fungi, animal cells and protozoa.
38. A cell transformed with the expression cassette of paragraph 35.
39. The cell according to paragraph 38, wherein said cell is selected from the group consisting of bacteria, fungi, yeast, plant cells, and animal cells.
40. A transformation vector having a polynucleotide which comprises a nucleotide sequence selected from the group of:
    a) the nucleotide sequence set forth in SEQ ID No. 1,
    b) a nucleotide sequence encoding the polypeptide set forth in SEQ ID No. 2;
    c) a nucleotide sequence encoding a polypeptide having at least 95% sequence identity to amino acid sequence SEQ ID No. 2, wherein the polypeptide exhibits herbicide-resistant AHAS activity;
    d) a nucleotide sequence having at least 85% identity to the nucleotide sequence set forth in SEQ ID No. 1, wherein the nucleotide sequence encodes a polypeptide comprising a large subunit of AHAS and exhibits herbicide-resistant AHAS activity;
    e) a nucleotide sequence fully complementary to one of the nucleotide sequences a) to (d); wherein the vector further comprises a selectable gene, at least one promoter operably linked to the nucleotide sequence capable of driving the expression of said nucleotide sequence.
41. Use of the vector of paragraph 40, for transforming cells selected from the group comprising bacteria, fungi, yeast, plant cells and animal cells.
42. A transformed plant, wherein said plant comprises at least one promoter integrated in its genome, which is operably linked to a polynucleotide selected from the group comprising:
    a) the nucleotide sequence set forth in SEQ ID No. 1,
    b) a nucleotide sequence encoding the polypeptide set forth in SEQ ID No. 2;
    c) a nucleotide sequence encoding a polypeptide having at least 95% sequence identity to amino acid sequence SEQ ID No. 2, wherein the polypeptide exhibits herbicide-resistant AHAS activity;
    d) a nucleotide sequence having at least 85% identity to the nucleotide sequence set forth in SEQ ID No. 1, wherein the nucleotide sequence encodes a polypeptide comprising a large subunit of AHAS and exhibits herbicide-resistant AHAS activity;
    e) a nucleotide sequence fully complementary to one of the nucleotide sequences a) to (d); wherein the vector further comprises a selectable gene, at least one promoter operably linked to the nucleotide sequence capable of driving the expression of said nucleotide sequence.
43. The plant according to paragraph 42, wherein the promoter is selected from the group consisting of a tissue-specific promoter and a chloroplast-specific promoter.
44. The plant according to paragraph 42, wherein the plant is a monocot.
45. The plant according to paragraph 42, wherein the plant is a dicot.
46. The plant according to paragraph 44, wherein the plant is selected from the group consisting of sorghum, corn, rice, and wheat.
47. The plant according to paragraph 45, wherein the plant is selected from the group consisting of soybean and oilseed rape.
48. The plant according to paragraph 42, wherein said plant comprises increased herbicide resistance as compared to the non-transformed plant.
49. The plant according to paragraph 42, wherein the herbicide is selected from the group consisting of imidazolinones and sulfonylureas.
50. A method for obtaining a herbicide-resistant plant or a plant with increased herbicide resistance, wherein said method comprises
    i) transforming a plant cell with an expression cassette or vector comprising a polynucleotide having a nucleotide sequence selected from the group of
    a) the nucleotide sequence set forth in SEQ ID No. 1;
    b) a nucleotide sequence encoding the polypeptide set forth in SEQ ID No. 2;
    c) a nucleotide sequence encoding a polypeptide having at least 95% sequence identity to amino acid sequence SEQ ID No. 2, wherein the polypeptide exhibits herbicide-resistant AHAS activity;
    d) a nucleotide sequence having at least 85% identity to the nucleotide sequence set forth in SEQ ID No. 1, wherein the nucleotide sequence encodes a polypeptide comprising a large subunit of AHAS and exhibits herbicide-resistant AHAS activity; and
    e) a nucleotide sequence fully complementary to one of the nucleotide sequences a) to d), wherein the expression cassette further comprises at least one promoter operably linked to the polynucleotide, wherein said promoter drives the expression of said polynucleotide;

ii) regenerating the plant cell to obtain a herbicide-resistant plant.

51. The method according to paragraph 50, wherein the promoter comprises a plant tissue-specific promoter.

52. The method according to paragraph 50, wherein the promoter comprises a chloroplast specific promoter.

53. The method according to paragraph 50, wherein the herbicide is selected from the group consisting of imidazolinone and sulfonylurea.

54. The method according to paragraph 53, wherein the imidazolinone herbicide is selected from the group comprising imazethapyr, imazapic, and imazapyr.

55. The method according to paragraph 50 wherein the plant is a monocot.

56. The method according to paragraph 50 wherein the plant is a dicot.

57. The method according to paragraph 55, wherein the plant is selected from the group consisting of sorghum, corn, rice, and wheat.

58. The method according to paragraph 56, wherein the plant is selected from the group consisting of soybean and oilseed rape.

59. The method according to paragraph 50, wherein said plant comprises increased herbicide resistance as compared to the non-transformed plant.

60. The method according to paragraph 50, wherein said plant comprises the large subunit of AHAS and exhibits herbicide-resistant AHAS activity.

This invention is better illustrated in the following examples, with should not be construed as limiting its scope. On the contrary, it should be clearly understood that other embodiments, modifications and equivalents of the invention may be possible after reading the present description, which someone skilled in the art could suggest without departing from the spirit of the present invention and/or the scope of the appended claims.

EXAMPLES

Example 1

Mutagenesis of Endogamic Sorghum Line 80237 and Selection of Imidazolinone-Resistant Mutant 80237EMS2-192

Thirty two thousand pre-germinated sorghum seeds from endogamic line 80237 were dipped into an aqueous solution of 0.05% v/v ethyl methanesulfonate (EMS) for 16 hours. Treated seeds were planted at the Experimental Station of Advanta Seeds in Venado Tuerto, Province of Santa Fe, Argentina, plot No. 1 (33° 41' 47" S; 61° 58' 45" W) on Dec. 21, 2007, and they were left for open pollination.

A total of 273 M1 plants were selected and two seeds from each plant were planted on May 23, 2008, at the Experimental Station of Advanta Seeds in Oran, Province of Salta, Argentina (22° 49' 37" S; 64° 20' 14" W) in a nursery and a total of 546 M2 plants was obtained. Pollen from one plant of each pair was collected and used for pollinating the other plant of the pair. M3 seeds obtained from each of the 273 pollinated M2 plants were harvested. A total of 273 furrows of M3 progeny were planted on Dec. 16, 2008, in Venado Tuerto and 50 plants from each M3 furrow were sprayed with 100 ml L a.i./ha of imazethapyr on Dec. 23, 2008. Sixty eight plants from the furrows showed normal growth and absence of symptoms after treatment with herbicide and were considered resistant to the herbicide and identified as VT09-9754. The genealogy of the resistant plants from the furrows was identified and they were designated 80237EMS2-192 (hereinafter referred to as ADV-IMI-R).

The generational history is shown in Table 5.

TABLE 5

| LOCATION-FURROW-SELECTION | GENERATION | GENEALOGY | PLANTING DATE |
|---|---|---|---|
| OR08-323-192 | M3 | 80237EMS2-192 | May 23, 2008 |
| VT09-9754-47 | M4 | 80237EMS2-192-47 | Dec. 16, 2008 |
| OR09-1305-1 | M5 | 80237EMS2-192-47-1 | May 28, 2009 |
| VT10-12793-2R | M6 | 80237EMS2-192-47-1 | Dec. 15, 2009 |
| VT11-11331-BK | M7 | 80237EMS2-192-47-1-2-(R) | Dec. 7, 2010 |

OR: Oran;
VT: Venado Tuerto

Example 2

Analysis of Response Rate to Treatment With Imidazolinones in Resistant ADV-IMI-R Mutant as Compared to the Original Sorghum Endogamic Line 80237

Sorghum line 80237 (Advanta's proprietary elite line) and imidazolinone-resistant ADV-IMI-R mutant of the present invention (original mutation) were sprayed on the field with three herbicides from the group of imidazolinones: imazethapyr, imazapyr, and imazapic. Four different rates were assayed for each of the herbicides: 1×, 2×, 3×, and 4× (being 1× the recommended application rate) (see Table 1 above):

Field experiments were carried out in Venado Tuerto, and planting took place on Dec. 1, 2010. The herbicide was sprayed 20 days after emergence (stage V6). All treatments were compared to their respective untreated controls. The experimental design consisted of plots divided into 3 replicates (main plot: treatment with herbicide; sub-plots: line).

Ten days after spraying, all plants were assayed for dry matter (DM) in aerial tissues. Herbicide response was assessed as a DM percentage in aerial tissue of the respective untreated control.

Thus, the line sensitive to herbicides i for each rate j was expressed as:

$$DM_{ij}\% \text{ Control} = (DM_{ij} * 100)/DM \text{ Control}$$

$DM_{ij}\%$ Control is the mean value of 3 experiments for each treatment from each line.

Example 3

Sequencing of a Sorghum AHAS Gene Encoding the Mutated Polypeptide of the Invention Having Acetohydroxyacid Synthase Activity and Which is Imidazolinone-Resistant Sequencing studies were made on leaf tissue from ADV-IMI-R mutant (VT11-11331-BK selection) and wild-type endogamic line 80237. Genomic DNA was isolated and resuspended in water at a final concentration of 100 ng/μl. Sequencing of the acetohydroxyacid synthase (AHAS) gene from ADV-IMI-R mutant and from sorghum line 80237, specific primers were designed for amplification by the polymerase chain reaction (PCR) based on the sorghum AHAS sequence disclosed in GenBank under Access No. GM663363.1. The primers were designed so as to generate 5 overlapping DNA segments (amplicons) representing the complete AHAS coding sequence. Sequences of designed primers are:

| | | |
|---|---|---|
| 1st amplicon (544 bp) | SbAHAS-F1 | CTCGCGCCGCCTCCGAGA (SEQ ID No. 5) |
| | SbAHAS-R1 | ATGCGCCGCGGAACCTGT (SEQ ID No. 6) |
| 2nd amplicon (579 bp) | SbAHAS-F2 | TGCTCGACTCCGTCC (SEQ ID No. 7) |
| | SbAHAS-R2 | CATCAAACCGCACACC (SEQ ID No. 8) |
| 3rd amplicon (511 bp) | SbAHAS-F3 | ATGCATGGCACGGTG (SEQ ID No. 9) |
| | SbAHAS-R3 | CAGCAGCCGGCAAAC (SEQ ID No. 10) |
| 4th amplicon (529 bp) | SbAHAS-F4 | CACAGGTGTTGGGCA (SEQ ID No. 11) |
| | SbAHAS-R4 | CTTGAAAGCCCCACCA (SEQ ID No. 12) |
| 5th amplicon (666 bp) | SbAHAS-F5 | GGAGCTAGCTATGATCCGAA (SEQ ID No. 13) |
| | SbAHAS-R5 | CAGAACCACTGCATAGCA (SEQ ID No. 14) |

The PCR mixture had a final volume of 25 µl and the following components: 1× reaction buffer (Invitrogen) 0.2 mM dNTPs (GE Healthcare), 2.5 mM $MgCl_2$ (Invitrogen), 0.2 µM of each primer, 0.5 µl Platinum Taq (5 U/µl) (Invitrogen) and 100 ng of genomic DNA. The PCR reaction was performed in a GeneAmp PCR System 9700 thermocycler (Perkin-Elmer) and amplification conditions were as follows: a step of initial denaturation at 94° C. for 1 minute followed by 35 cycles at 94° C. for 45 seconds, 57° C. for 45 seconds, and 72° C. for 70 seconds, and a final elongation step at 72° C. for 10 minutes.

No amplification products were obtained when the SbAHAS-F1 and SbAHAS-R1OLD1-R2 primers were used, both with ADV-IMI-R products as well as the original sorghum line 80237.

In order to overcome this problem, two new primers were designed to generate a sixth amplicon:

| | | |
|---|---|---|
| 6th amplicon (6289 bp) | SbAHAS-F1-2 | TCGAGGCTCTTGAGCGCTG (SEQ ID No. 15) |
| | SbAHAS-R1-2 | ATGCGCCGCGGAACCTGT (SEQ ID No. 16) |

The same PCR conditions as those described above were used to obtain the 6th amplicon.

Two µl of each DNA product resulting from amplification by PCR were examined by agarose gel electrophoresis to analyze fragment sizes and estimated DNA concentration with reference to the molecular weight marker Low DNA Mass Ladder (Invitrogen). The remaining PCR products were purified using Wizard® SV gel (Promega) and *PCR Clean-Up System* (Promega). Purified DNA was sequenced using BigDye® Terminator v3.1 *Cycle Sequencing System* (Applied Biosystems) according to the manufacturer's instructions.

Sequencing files for acetohydroxyacid synthase obtained with each amplicon were assembled using *CAP3 Sequence Assembly Program* (http://pbil.univ-lyon1.fr/cap3.php). The resulting DNA sequences of the acetohydroxyacid synthase gene were aligned using the Clustal W version 2.1 program (http://www.clustal.org).

Example 4

Inheritance of Imazethapyr Resistance in a Segregating F2 Sorghum Population Generated by Crossing an Imazethapyr-Susceptible Line With the Resistant ADV-IMI-R Mutant A targeted crossing was carried out between sorghum line 90523 (Advanta proprietary elite line, susceptible to imidazolinones) and the imidazolinone-resistant ADV-IMI-R mutant (VT09-9754-48-6-BK selection). The resulting F1 plants were auto-pollinated and F2 seeds were harvested. The F2 seeds were planted in the field in Venado Tuerto, in October 2010. The F2 plants (177 plants) were sprayed with imazethapyr (Pivot®, BASF) at a rate of 3× (where 1× is the rate recommended by the manufacturer for commercial use which is equivalent to 100 ml a.i./ha). Before spraying, leaf tissue from each of the 177 F2 plants from both ADV-IMI-R mutant (VT09-9754-48-6-BK selection) and wild-type line 90523 were collected to isolate genomic DNA, which was resuspended in water at a final concentration of 100 ng/µl for use in genotypic analysis.

Herbicide was sprayed 20 days after emergence (stage V6). The plants were assessed ten days after spraying, and the herbicidal effect was classified into three categories by visually assessed symptoms according to the following phenotypic scoring:
1=no damage
2=chlorotic
3=death Example 5

Development of DNA Markers Specific for SNP-SbAHAS

A single point mutation in the AHAS gene replacing nucleotides G by A at nucleotide position +277 (codon 93) distinguishes the original endogamic sorghum line 80237 (herbicide-susceptible) from the induced ADV-IMI-R mutant. A molecular marker (designated herein as SNP-SbAHAS) was designed using the following group of dual labeled primers and probes:

| Primer/Probe | Sequence | Modification |
|---|---|---|
| Forward primer | CCGCGACGTCTTCGC (SEQ ID No. 17) | — |
| Reverse primer | TGCCTGGTGGATCTCCAT (SEQ ID No. 18) | — |
| Probe 1 | TACCCCGGCGGCACG (SEQ ID No. 19) | 5'FAM-3'BHQ |
| Probe 2 | TACCCCGGCGGCGCG (SEQ ID No. 20) | 5'VIC-3'BHQ |

Genotyping was performed by a real time PCR allelic discrimination assay using an AB 7500 thermocycler (Applied Biosystems, Foster City, Calif., US). A PCR reaction mix was prepared in a final volume of 25 µl comprising: 12.5 µl 2× Perfecta® qPCR Supermix (Quanta Biosciences, Gaithersburg, Md., US), 0.08 µM primers (forward and reverse), 0.4 µM probes (1 and 2), 10 µl genomic DNA and DNase-free water to make up the final volume. Amplification conditions: one initial denaturation cycle at 95° C. for 10 min, followed by 50 denaturation cycles at 92° C. for 15 seconds and hybridization/extension at 60° C. for 1 min. The results of the allelic discrimination assay were analyzed after amplification using the AB Sequence Detection System (SDS) 7500 1.4 software program (Applied Biosystems, Foster City, Calif., US).

Example 6

Correlating Herbicide Resistance with AHAS Mutation in ADV-IMI-R Mutants

Individual F2 progeny plants obtained by a ADV-IMI-R× 90523 crossing were phenotypically classified (no damage, chlorosis and death) after spraying with imazethapyr (using the method of Example 4) and then genotypically classified using the molecular marker SNP-SbAHAS which is specific of the induced mutation in AHAS (using the method described in Example 5).

Example 7

Genetic Mapping of Herbicide-Resistance and the Specific SNP-SbAHAS Marker

Herbicide-resistance and the specific SNP-SbAHAS marker were genetically mapped. Based on the sorghum AHAS sequence disclosed in GenBank (Access No. GM663363.1, a BLAST analysis was carried out matching it with *Sorghum bicolor* genomic DNA sequences deposited in the Phytozome database (http://www.phytozome.net/search.php).

Genotyping (fingerprinting) of the mutated ADV-IMI-R line and the endogamic line 90253 was carried out using a group of SSR-type molecular markers. Seven polymorphic SSRs located in chromosome 4 of *Sorghum bicolor* genome were selected for genotyping (Mace, E S et al., *A consensus genetic map of sorghum that integrates multiple component maps and high-throughput Diversity Array Technology (DArT) markers*, BMC Plant Biology, 2009, 9: 13; Srinivas, G et al., *Exploration and mapping of microsatellite markers from subtracted drought stress ESTs in Sorghum bicolor* (L.), Moench. Theor. Appl. Genet. 2009, 118: 703-717; Ramu, P et al., *In silico mapping of important genes and markers available in the public domain for efficient sorghum breeding*, Mol Breeding 2010, 26: 409-418; http://www.lbk.ars.usda.gov/psgd/sorghum/2009SorghumSEAMs_LB KARS.xls)

The 7 selected polymorphic SSRs were:

| SSR in chromosome 4 | Forward primer | Reverse primer |
| --- | --- | --- |
| Xtxp12 | AGATCTGGCGGCAACG (SEQ ID No. 21) | AGTCACCCATCGATCATC (SEQ ID No. 22) |
| Xtxp177 | GCCGGTTGTGACTTG (SEQ ID No. 22) | TTAAAGCGATGGGTGTAG (SEQ ID No. 24) |
| Xtxp343 | CGATTGGACATAAGTGTTC (SEQ ID No. 25) | TATAAACATCAGCAGAGGTG (SEQ ID No. 26) |
| Dsenhsbm39 | TCAGTGATACAGCCGTCCAG (SEQ ID No. 27) | ATGCATAAACCACGGCTGTC (SEQ ID No. 28) |
| Xgap010 | GTGCCGCTTTGCTCGCA (SEQ ID No. 29) | TGCTATGTTGTTTGCTTCTCCCTTCTC (SEQ ID No. 30) |
| Xsbarslbk4.50 | GTGAAGCATCCCAACCCTTA (SEQ ID No. 31) | GCCTTTTTCCGTCTTCGAG (SEQ ID No. 32) |
| Xsgarslbk4.13 | TCGGGTATTAGCCCTTTGTG (SEQ ID No. 33) | ACACCTCCTCTTGGTGGATG (SEQ ID No. 34) |

The resulting PCR fragments from each of the tested SSRs were resolved by capillary electrophoresis using an automated sequencer ABI3130×1 (Applied Biosystems). Genotyping of these 7 SSRs was carried out in 177 individuals of the F2 progeny resulting from the ADV-IMI-R× 90523 crossing. In addition, these same 177 F2 progeny plants were analyzed as to the presence of the SNP-SbAHAS marker specific for the induced mutation in the AHAS gene. The results were classified according to phenotypic rating upon application of imazethapyr on F2 progeny plants and analyzed using the computer program JoinMap (Van Ooijen, J W and Voorips, R E, JoinMap 3.0 Software for the calculation of genetic linkage maps, Plant Research International, 2001, Wageningen, The Netherlands).

The invention claimed is:

1. A method for identifying a sorghum herbicide-resistant plant, comprising:
   a) providing a nucleic acid sample from a non-transgenic sorghum plant;
   b) amplifying a region corresponding to the AHAS gene present in said nucleic acid sample from a sorghum plant;
   c) identifying a herbicide-resistant sorghum plant based on the presence of one mutation in the amplified nucleic acid sample, where said mutation confers resistance to herbicides from the imidazolinone group, wherein said one mutation comprises an Ala93Thr substitution in an encoded polypeptide, wherein said polypeptide has acetohydroxyacid synthase activity, and wherein the nucleic acid sample comprises SEQ ID No. 1; and
   d) applying one or more imidazolinone herbicides to the identified herbicide-resistant sorghum plant, wherein the sorghum plant has increased resistance to one or more imidazolinone herbicides as compared to wild-type sorghum plants.

* * * * *